(12) United States Patent
Coe, Jr. et al.

(10) Patent No.: US 11,848,094 B2
(45) Date of Patent: Dec. 19, 2023

(54) MULTIDIMENSIONAL OPTICAL TISSUE CLASSIFICATION AND DISPLAY

(71) Applicants: IR MEDTEK LLC, Gahanna, OH (US); OHIO STATE INNOVATION FOUNDATION, Columbus, OH (US)

(72) Inventors: James V. Coe, Jr., Dublin, OH (US); Rebecca C. Bradley, Gahanna, OH (US)

(73) Assignees: Ohio State Innovation Foundation, Columbus, OH (US); IR Medtek LLC, Gahanna, OH (US)

( * ) Notice: Subject to any disclaimer, the term of this patent is extended or adjusted under 35 U.S.C. 154(b) by 0 days.

(21) Appl. No.: 17/658,489

(22) Filed: Apr. 8, 2022

(65) Prior Publication Data

US 2023/0326578 A1 Oct. 12, 2023

(51) Int. Cl.
*G16H 30/20* (2018.01)
*G06N 20/00* (2019.01)

(52) U.S. Cl.
CPC ............ *G16H 30/20* (2018.01); *G06N 20/00* (2019.01)

(58) Field of Classification Search
CPC .............................. G16H 30/20; G06N 20/00
See application file for complete search history.

(56) References Cited

U.S. PATENT DOCUMENTS

| | | |
|---|---|---|
| 5,596,992 A | 1/1997 | Haaland et al. |
| 6,146,897 A | 11/2000 | Cohenford et al. |
| 6,620,621 B1 | 9/2003 | Cohenford et al. |
| 6,841,388 B2 | 1/2005 | Dukor et al. |
| 7,280,866 B1 | 10/2007 | McIntosh et al. |

(Continued)

FOREIGN PATENT DOCUMENTS

| | | |
|---|---|---|
| WO | WO-2016022595 A1 | 2/2016 |
| WO | WO-2017161097 A1 | 9/2017 |

OTHER PUBLICATIONS

Andleeba, Farah, et al., "Attenuated total reflectance spectroscopy to diagnose skin cancer and to distinguish different metastatic potential of melanoma cell", Cancer Biomarkers 23 DOI 10.3233/CBM-181393, (2018), 9 pages.

(Continued)

*Primary Examiner* — Michael Tomaszewski
*Assistant Examiner* — William T. Monticello
(74) *Attorney, Agent, or Firm* — Schwegman Lundberg & Woessner, P.A.

(57) ABSTRACT

Mid-infrared spectroscopic analysis of tissue specimens can include training a learning model and using the trained learning model to classify tissue into at least two (or more than two) categories such as a tumor category, a non-tumor category, and a histology category. Resulting richer diagnostic indication can be provided and can optionally be mapped to a schema for RGB or other display. Efficient and accurate classification can employ an efficient linear SVM model representation. The model representation can include a $\beta$ spectrum including the fuller wavelength set, a central tendency indicator ($\mu$) of the training set, a spread indicator ($\sigma$) of the training set, and a scaling factor. Various types of illuminators and response detectors can include one or more Quantum Cascade Lasers, broadband light source configured to permit spectral separation, a thermal or other imaging array, among others.

29 Claims, 12 Drawing Sheets

(56) References Cited

U.S. PATENT DOCUMENTS

| | | |
|---|---|---|
| 8,502,148 B2 | 8/2013 | Wagner et al. |
| 8,780,347 B2 | 7/2014 | Kotidis et al. |
| 8,981,298 B2 | 3/2015 | Wagner et al. |
| 9,003,869 B2 | 4/2015 | Wagner et al. |
| 9,329,085 B2 | 5/2016 | Kotidis et al. |
| 9,606,002 B2 | 3/2017 | Bird et al. |
| 9,683,922 B2 | 6/2017 | Wagner et al. |
| 10,031,077 B2 | 7/2018 | Kotidis et al. |
| 10,139,349 B2 | 11/2018 | Kapelushnik et al. |
| 10,175,159 B2 | 1/2019 | Wagner et al. |
| 10,643,832 B2 | 5/2020 | Eberlin et al. |
| 2001/0020132 A1 | 9/2001 | Nordstrom |
| 2004/0162489 A1 | 8/2004 | Richards-Kortum et al. |
| 2010/0130868 A1 | 5/2010 | Hargrove et al. |
| 2012/0122084 A1 | 5/2012 | Wagner et al. |
| 2012/0196356 A1 | 8/2012 | Wagner et al. |
| 2012/0199741 A1 | 8/2012 | Wagner et al. |
| 2012/0199742 A1 | 8/2012 | Wagner et al. |
| 2012/0202277 A1 | 8/2012 | Wagner et al. |
| 2012/0202278 A1 | 8/2012 | Wagner et al. |
| 2012/0204628 A1 | 8/2012 | Wagner et al. |
| 2012/0225474 A1 | 9/2012 | Wagner et al. |
| 2012/0328178 A1* | 12/2012 | Remiszewski et al. |
| 2013/0292571 A1 | 11/2013 | Mukherjee et al. |
| 2014/0316255 A1 | 10/2014 | Garai et al. |
| 2015/0292947 A1 | 10/2015 | Kotidis et al. |
| 2016/0045113 A1 | 2/2016 | Lorence |
| 2016/0310023 A1 | 10/2016 | Chachisvilis et al. |
| 2017/0281077 A1 | 10/2017 | Pyun et al. |
| 2018/0055368 A1 | 3/2018 | Noto et al. |
| 2018/0085004 A1 | 3/2018 | Pyun et al. |
| 2018/0206780 A1 | 7/2018 | Pyun et al. |
| 2019/0246971 A1* | 3/2019 | Pyun et al. |
| 2019/0110687 A1* | 4/2019 | Coe et al. |
| 2019/0156159 A1* | 5/2019 | Kopparapu |
| 2019/0261913 A1* | 8/2019 | Beaulieu et al. |
| 2021/0169336 A1* | 6/2021 | Sanchez et al. |

OTHER PUBLICATIONS

Berisha, Sebastian, et al., "Deep learning for FTIR histology: leveraging spatial and spectral features with convolutional neural networks", Analyst doi:10.1039/c8an01495g, (Feb. 25, 2019), 31 pages.

Chekkoury, Andrei, et al., "Automated Malignancy Detection in Breast Histopathological Images", Proc. of SPIE vol. 8315 831515-1, (2012), 13 pages.

Chen, Zhaomin, et al., "Infrared Metrics for Fixation-Free Liver Tumor Detection", dx.doi.org/10.1021/jp4073087 J. Phys. Chem. B 117, (Sep. 20, 2013), 9 pages.

Coe, James V., et al., "Imaging infrared spectroscopy for fixation-free liver tumor detection", Proc. of SPIE vol. 8947 89470B-1, (2014), 6 pages.

Fernandez, Daniel, "Infrared spectroscopic imaging for histopathologic recognition", Nature Biotechnology vol. 23 No. 4, (Apr. 2005), 7 pages.

Hu, Chengxu, et al., "Raman spectra exploring breast tissues: Comparison of principal component analysis and support vector machine-recursive feature elimination", Med. Phys. 40 (6), Jun. 2013 0094-2405/2013/40(6)/063501/7, (Jun. 2013), 8 pages.

Kyriakidou, Maria, et al., "FT-IR Spectroscopy Study in Early Diagnosis of Skin Cancer", in vivo 31: 1131-1137, (2017), 7 pages.

Widjaja, Effendi, et al., "Classification of colonic tissues using near-infrared Raman spectroscopy and support vector machines", International Journal of Oncology 32: 653-662, (2008), 10 pages.

* cited by examiner

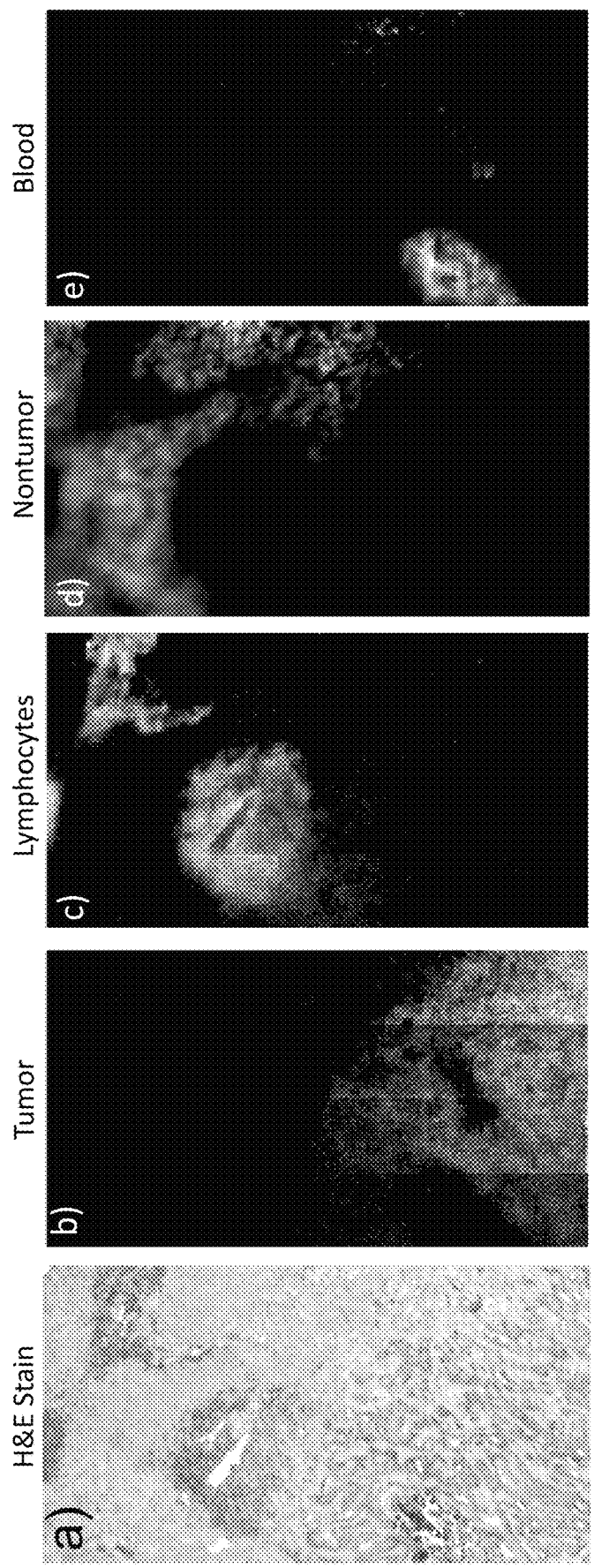

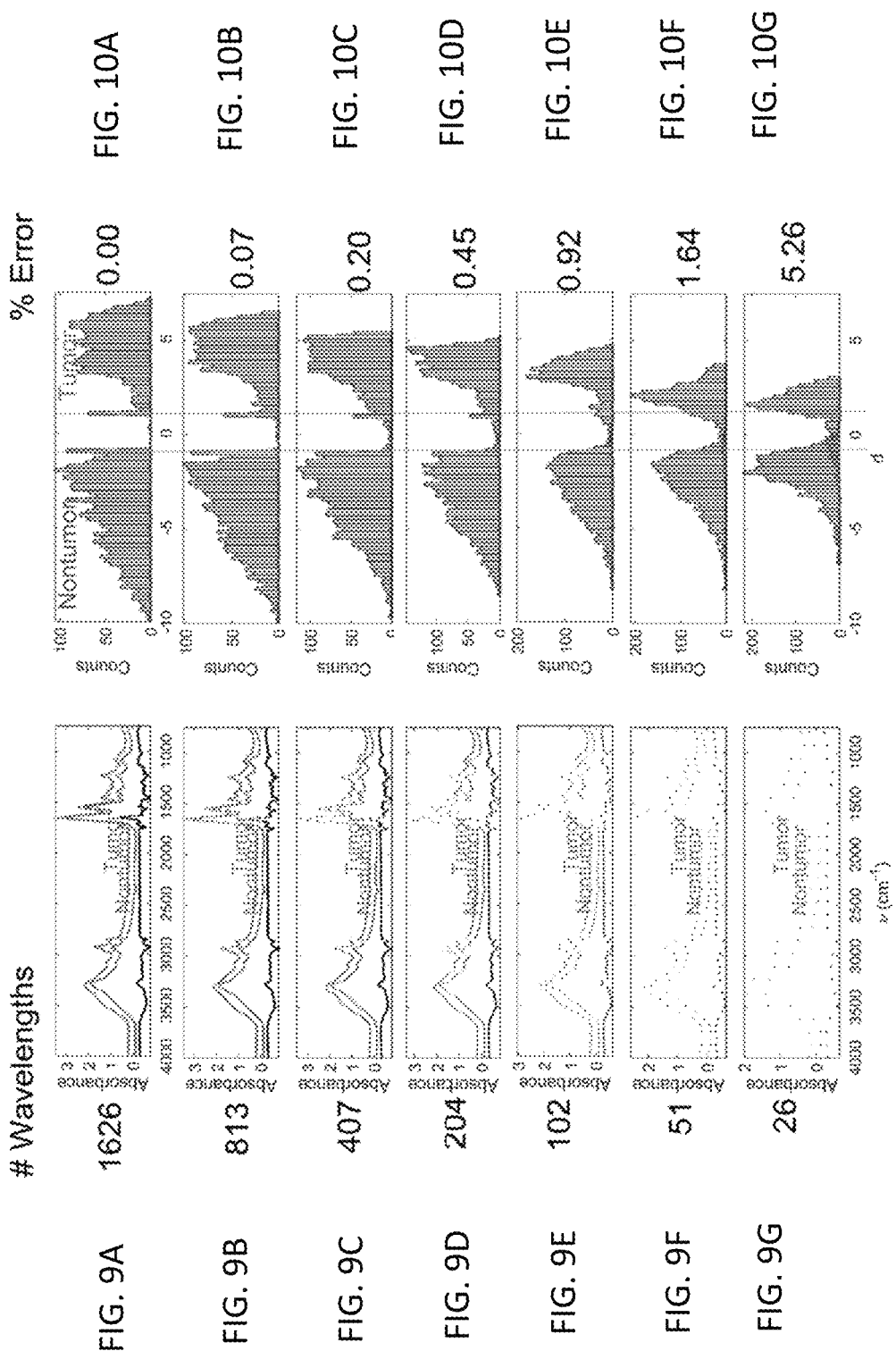

MULTIDIMENSIONAL OPTICAL TISSUE CLASSIFICATION AND DISPLAY

Coe et al. U.S. Patent Application Publication No. US 2019/0110687 A1 entitled SYSTEM AND METHOD FOR THE DISCRIMINATION OF TISSUES USING A FAST INFRARED CANCER PROBE, which is hereby incorporated herein by reference, and which published on Apr. 18, 2019, relates to using an infrared probe and discriminating software to rapidly discriminate normal non-cancerous tissue from abnormal cancerous tissue.

BACKGROUND

Technical Field

This document pertains generally, but not by way of limitation, to techniques for multidimensional optical and other electromagnetic spectroscopic tissue classification.

SUMMARY

Mid-infrared spectroscopic analysis of tissue specimens can include training a learning model and using the trained learning model to classify tissue into at least two (or more than two) categories such as a tumor category, a non-tumor category, and a histology category. Resulting richer diagnostic indication can be provided and can optionally be mapped to a schema for RGB or other display. Efficient and accurate classification can employ an efficient linear SVM model representation. The model representation can include a $\beta$ spectrum including the fuller wavelength set, a central tendency indicator ($\mu$) of the training set, a spread indicator ($\sigma$) of the training set, and a scaling factor. Various types of illuminators and response detectors can include one or more Quantum Cascade Lasers, a broadband light source with spectral separation, a thermal or other imaging array, among others.

The present inventors have recognized, among other things, a need to efficiently and accurately provide richer diagnostic information, such as which can be timely presented to a diagnostician or clinician in an easier to understand manner, such as to help support diagnostic or clinical decisions regarding tissue samples being examined or excised or otherwise treated, whether in a pathology lab, in an operating room (e.g., to help provide an in vivo indication of surgical margin), in a primary care office, or in another setting. Optical or other electromagnetic spectroscopies can be used to classify tissue. This can include illuminating a tissue sample using infrared (IR) electromagnetic energy illumination wavelengths, such as using an Attenuated Total Reflection (ATR) probe, using a Fourier Transform IR Attenuated Total Probe (FTIR-ATR, or "FTIR") probe or a fiber loop probe or other probe, using one or more tunable Quantum Cascade Lasers (QCLs), or using a broadband light source configured to allow spectral separation, or other illumination technique, such as described herein. As an illustrative example of another illumination technique, a QCL frequency comb arrangement can be used to provide spectral separation of light before delivery to and illumination of a desired location of a specimen. Two frequency combs or other paired, discrete infrared light sources can be used with a heterodyne detection scheme for high accuracy measurements of the signal.

An absorbance, reflection, scattering, fluorescence, Raman, or other electromagnetic energy response signal from the tissue sample or specimen can be imaged or otherwise detected or acquired, such as using a bolometer or other photodetector, using a thermal microbolometer array detector or a Focal Plane Array (FPA) imaging array detector or other array of photodetector pixels, using the ATR or FTIR probe, using diffuse reflectance IR, or other acquisition technique. The response from the tissue sample can be analyzed using spectroscopic techniques, such as described herein, that can be efficiently and accurately provide richer diagnostic information, such as which can be timely presented to a diagnostician or clinician in an easier to understand manner. For example, the techniques described herein can be used not only to efficiently distinguish between cancerous (e.g., tumor) and non-cancerous (e.g., "normal") tissue, but to also classify the tissue sample according to another dimension, such as into a histology category that is different from a tumor category and different from a non-tumor category. As illustrative examples, such a histology category can include one or more subcategories, such as one or more of wherein the histology category includes at least one of the following histology subcategories: a blood-dominated tissue histology subcategory; a non-blood-dominated tissue histology subcategory; a basal tissue histology subcategory; a squamous tissue histology subcategory; a lymphocyte-rich tissue histology subcategory; a non-lymphocyte-rich tissue histology subcategory; a keratinous tissue histology subcategory; or a non-keratinous tissue histology subcategory.

More generally, the present techniques can permit classifying one or more locations of the tissue sample or specimen into at least one of at least three categories including (1) a tumor category; (2) a non-tumor category; and (3) a histology category that is different from a tumor category and different from a non-tumor category. One or more indications of this additional richer information can be presented to a diagnostician or clinician, such as using one or more particularly useful user interface (UI) display techniques, such as described herein. The analysis techniques can benefit from efficient and accurate signal processing, such as using a trained learning model, such as which can be specially adapted for tissue classification, such as into at least one of at least three categories—although the present trained learning model techniques can also be advantageous for tissue classification into at least one of two categories, such as tumor and non-tumor, if desired.

The richer information provided by the present techniques can benefit from efficient and accurate signal processing by the trained learning model, such as to help provide timely results to the diagnostician or clinician, and can also benefit from efficient and accurate training of the learning model itself. In particular, training of the model can involve processing considerable amounts of information in training sets used for training the model. For example, the training can involve using a fuller wavelength set, relative to a reduced wavelength set for delivering the illuminating electromagnetic energy to the specimen. However, using the present techniques, the trained learning model that is used for tissue specimen response evaluation to delivering the illuminating electromagnetic energy to the specimen for the classifying and the providing the tissue output classification indication can allow the illumination to the specimen to use a reduced wavelength set relative to the fuller wavelength set used for the training.

For example, the training of the learning model can involve using linear Support Vector Machines (SVM) techniques to develop and represent decision equations for classifying one or more locations of the tissue specimen. Using linear SVM can yield a more simple-to-apply resulting trained learning model than non-linear SVM. Also, the resulting trained linear SVM learning model can be more robust to noise or other perturbations as compared to a non-linear SVM trained learning model.

In an example, the linear SVM model representation can include an SVM R spectrum including a fuller wavelength set (as compared a reduced set of wavelengths used for illuminating the tissue sample during sample evaluation); (2) a central tendency indicator (μ) of the training set; (3) a spread indicator (σ) of the training set; and (4) a scaling factor. In an example, the trained linear SVM model can be represented as:

$$d_k = b + \left\langle \left|\frac{Test_{k,j} - \overline{Train}_j}{\sigma_{Train_j}}\right| \beta_j \right\rangle, \text{ where } \beta_j = \sum_i \alpha_i y_i \left(\frac{SV_{i,j} - \overline{Train}_j}{\sigma_{Train_j}}\right),$$

wherein $d_k$ represents one of k decision equation value or other classifier criteria, b is an offset constant, $\beta_j$ is referred to as a "beta spectrum", $\overline{Train}_j$ (with the bar drawn over) represents an average of a training set, and $\sigma_{Train_j}$ represents a standard deviation or other spread indicator of the training set.

In this way, the trained linear SVM learning model can advantageously be arranged to represent the SVM decision equations so that the results can be output as three IR spectra and a constant: the SVM β spectrum, the average of the training spectra, the standard deviation of the training spectra, and a bias or offset constant. This efficient representation allows SVM decision equation values to be determined without the training software and without the need to output all of the support vectors (otherwise usually hundreds of support vectors, in this tissue classification application, and each is a full IR spectrum). The process of SVM can be optimized upon choice of data in the desired decision region. This allows the present techniques to provide an optimal decision/categorization hypersurface, such as for separating measurements into two categories, such as tumor and non-tumor, or multiple categories, such as four categories, or another number of categories, such as explained herein.

Thus, the present techniques permit the learning model to be trained using a fuller wavelength set, relative to a reduced wavelength set for delivering the illuminating electromagnetic energy to the specimen. Delivering the illuminating electromagnetic energy to the specimen for the classifying and the providing of the tissue output classification indication can use a reduced wavelength set relative to the fuller wavelength set used for training the learning model. For example, delivery of the illuminating electromagnetic energy to the tissue specimen can include at least one of selecting or tuning at least one of a Quantum Cascade Laser (QCL) or broadband light source configured to permit spectral separation. In an example, the reduced wavelength set for illuminating the sample is specified to correspond to wavelengths falling within an output wavelength range of a selectable tunable QCL (or broadband light source configured to permit spectral separation) or within an output wavelength range of a single tunable QCL (or broadband light source configured to permit spectral separation across an output wavelength range).

Another aspect of the present techniques, such as providing an improved trained learning model for use in tissue discrimination or classification, can involve inhibiting an effect of water vapor or other gas phase interference on the training of the learning model. This can include modifying the spectral data of the training set for training the learning model, such as can include pre-processing of spectral data of the fuller wavelength set using a second derivative of the spectral data across wavenumbers of the fuller wavelength set, used for training, before determining the linear SVM model representation. Such pre-processing using the second derivative of the spectral data can help to inhibit an effect of water vapor or other gas phase interference that may otherwise interfere with using the trained model for evaluating specimen response from the reduced set of illumination wavelengths.

Further, such pre-processing can include performing the second derivative of the spectral data across wavenumbers of the fuller wavelength set but skipping one or more steps of wavenumbers for performing the second derivative. For example, such skipping wavenumbers can include skipping between 1 and 20 steps of wavenumbers between steps of wavenumbers selected for performing the second derivative, as explained further herein. Doing so can help to inhibit an effect of water vapor or other gas phase interference that may otherwise interfere with using the trained model, as explained herein.

Another aspect of the present techniques can include advantageously presenting a helpful visual representation of the classification to the diagnostician, clinician, or other user. In an illustrative example, electromagnetic energy response data from different locations of the specimen can be received at an imaging focal plane array (FPA). The FPA can include pixels corresponding to the electromagnetic energy response data from the different locations of the specimen. The tissue classification can include classifying individual pixels using the trained learning model to categorize an individual pixel into one of the at least three categories. Resulting information can be displayed or otherwise provided to the user, such as via an output pixel array. For example, the displayed information can include a color imaging representation of the classified individual pixels, using different colors of individual pixels in the output pixel array to represent the different ones of the categories. An intensity indication of the individual pixels in the output pixel array can be used to represent classification strength information from the trained learning model. The displayed image can advantageously be configured to be comparable to an H&E histopathological stain representation, such as can be interpreted by a pathologist. However, the displayed image can advantageously be signal processed to present displayed information in an even more informative manner than an H&E histopathological stain representation, such as by color or shading representation of different types of tissue categorizations beyond what is typically available in an H&E histopathological stain representation, by segmenting displayed regions of the tissue specimen to emphasize differences in categorization and to help provide a deeper interpretation and understanding of the data being presented. As an illustrative example described further herein, the multi-dimensional spectral tissue classification, such as performed using the techniques described herein, can be used to present a displayed color image differentiating between tissue specimen regions corresponding to non-tumor regions (e.g., represented by the displayed color green), lymphocyte-rich regions (represented by the displayed color blue), tumor regions (represented by the displayed color red) and blood-rich regions (represented by the displayed color yellow).

Because of the efficiency of the trained model representation, and the enhanced accuracy (such as via the pre-processing of spectral data for training the model), and the richer and more flexible categorization capability, more useful information can be timely presented to the user. Such information can even be displayed on a real-time basis, if desired, which can provide useful guidance, such as in the operating room during surgery or laparoscopic, arthroscopic, or other endoscopic or other "minimally invasive" clinical treatment.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 7A-7E show an example of an H&E stain image (FIG. 7A), placed side-by-side with RGB decision equation displayed images of the same specimen having a tumor (FIG. 7B), having lymphocytes (FIG. 7C), having non-tumor (FIG. 7D), and having blood (FIG. 7E).

FIGS. 9A-9G and corresponding FIGS. 10A-10G show spectral absorbance vs. frequency data (FIGS. 9A-9G), with corresponding histogram data (FIGS. 10A-10G), as wavelengths are reduced from 1626 wavelengths (FIG. 9A, FIG. 10A), to 813 wavelengths (FIG. 9B, FIG. 10B), 407 wavelengths (FIG. 9C, FIG. 10C), 204 wavelengths (FIG. 9D, FIG. 10D), 102 wavelengths (FIG. 9E, FIG. 10E), 51 wavelengths (FIG. 9F, FIG. 10F), and 26 wavelengths (FIG. 9G, FIG. 10G).

DETAILED DESCRIPTION

Mid-infrared spectroscopic analysis of tissue specimens can include training a learning model and using the trained learning model to classify tissue into at least two (or more than two) categories such as a tumor category, a non-tumor category, and a histology category. Resulting richer diagnostic indication can be provided and can optionally be mapped to a schema for RGB or other display. Efficient and accurate classification can employ an efficient and easy-to-apply linear SVM model representation, or a non-linear SVM model representation can be used, if desired. The linear SVM model representation can include a β spectrum including the fuller wavelength set, a central tendency indicator (μ) of the training set, a spread indicator (σ) of the training set, and a scaling factor. Various types of illuminators and response detectors can include one or more Quantum Cascade Lasers, broadband light source configured to permit spectral separation, a thermal or other imaging array, among others.

Figure 1:
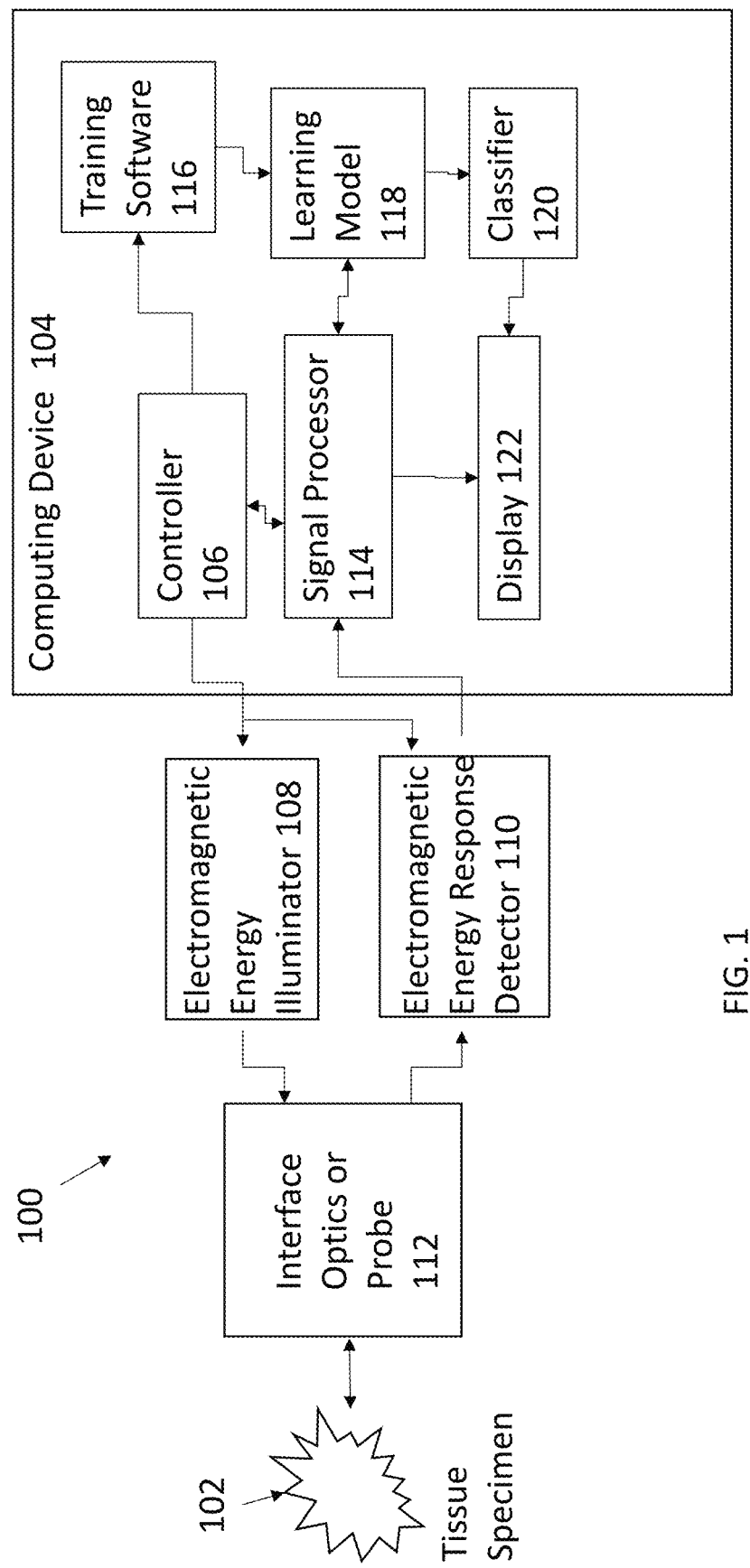
FIG. 1 is a schematic diagram illustrating generally an example of portions of a system, such as can be used for classifying a tissue specimen.

FIG. 1 is a schematic diagram illustrating generally an example of portions of a system 100, such as can be used for classifying a tissue specimen 102. The system 100 can include a computing device 104. The computing device 104 can include or be coupled to a controller 106. The controller 106 can be configured to provide one or more control output signals, such as to control an electromagnetic energy illuminator 108 and an electromagnetic energy response detector 110, which can be separate components or can be integrated together in a shared component. The illuminator 108 and the response detector 110 can interface with the tissue specimen 102 via one or more of a fiber optic cable or other interface optics or probe component 112. For example, the response detector 110 can include a photodetector or a Focal Plane Array (FPA) imaging array of pixels, either of which can transduce the response signal into a suitable electrical signal that can be digitized and stored in memory or buffer circuitry and provided to a signal processor 114 such as which can be included in or coupled to the computing device 104. As explained herein, the computing device 104 can include training software 116, such as can be used to train a learning model 118 such as which can be stored in memory circuitry included in or communicatively coupled to the computing device 104. The training model 118 can be included in or coupled to a classifier 120, such as can be used to classify one or more locations on the tissue specimen 102 into two or more (or three or more, as described herein) different categories. The classification by the classifier 120 can be displayed to a diagnostician, clinician, or other user, such as via a local or remote display 122, such as can be included in or coupled to the computing device 104. In an example, the classification information can be displayed on an enhanced image of portions of the tissue specimen 102, such as can be acquired via the response detector 110 or another imaging device such as can be arranged to gather one or more images from the tissue specimen 102.

The illuminator 108 can be configured for including or using an Attenuated Total Reflection (ATR) probe, using a Fourier Transform IR Attenuated Total Probe (FTIR-ATR, or "FTIR") probe, using one or more tunable Quantum Cascade Lasers (QCLs), or using a broadband light source configured to permit spectral, or other illumination technique, such as described herein. The response detector 110 can be configured for acquiring, detecting, or imaging one or more of a reflection, scattering, fluorescence, Raman, or other electromagnetic energy response signal from the tissue sample or specimen 102. The response detector 110 can be configured for including or using a photodetector, using a Focal Plane Array (FPA) imaging array detector, using the ATR or FTIR probe, using diffuse reflectance IR, or other acquisition technique.

A. Acquisition of Training Set and Training Learning Model (Overview)

Figure 2:
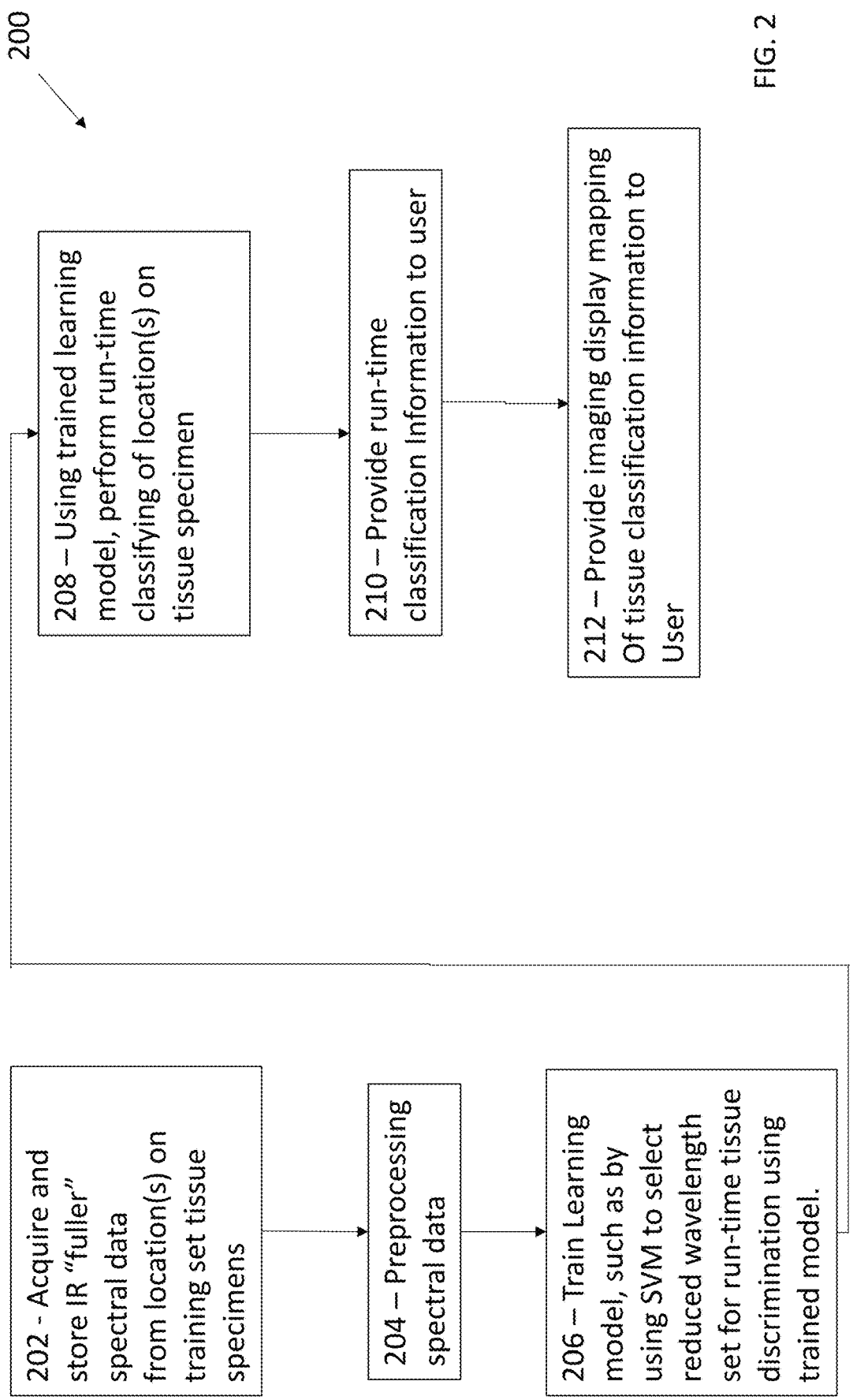
FIG. 2 is a flow chart illustrating generally an example of portions of a technique that can include a method of training and using a learning model for performing tissue classification into at least two, or more than two tissue classification categories.

FIG. 2 is a flow chart illustrating generally an example of portions of a technique that can include a method 200 of training and using a learning model 118, such as using training software 116 on a computing device 104 to direct the controller 106 for operating the illuminator 108 and the response detector 110 for acquiring IR spectral data from a training set of tissue specimens 102. For example, the training set of tissue specimens can include in vivo or resected tissue samples from one or more or a population or sub-population of human or animal subjects, appropriately preserved, such as by freezing the tissue samples or the like.

At 202, "fuller" IR spectral data can be acquired from one or more locations on one or more tissue specimens of the training set, and the acquired spectral data can be stored, such as in a memory or database, such as for training the learning model 118. For training the learning model 118, "fuller" wavelength set (e.g., higher spectral resolution spectral data) can be acquired and used for training, as opposed to a "reduced" wavelength set usable by the trained learning model 118 at run-time for quickly and accurately performing multidimensional tissue classification into two or more, three or more, or many multidimensional tissue classification categories, such as described herein.

As an illustrative example, a practical probe can be used with an FTIR system having an illuminator 108 and response detector 110 and may have a resolution of 4 $cm^{-1}$ over a wavelength range from 900 $cm^{-1}$ to 1800 $cm^{-1}$, yielding a response at 450 different wavenumber values (2 $cm^{-1}$ steps) for use in training the learning model 118. When appropriately trained, such as using the techniques described herein, it may be possible to greatly reduce the number of wavenumbers used to classify tissue specimens at run-time using the trained learning model 118, such as by using 10 or fewer selected wavelengths (e.g., ~5 wavelengths) for operating the illuminator 108 and as the response detector 110 at run-time for multi-dimensional tissue classification. The IR spectral range used for training may include certain spectral bands of particular interest for tissue discrimination, such as spectral bands corresponding to the amide I, amide II, amide III, and amide IV bands of protein, or the like, such as described at least in part in Coe et al. U.S. Patent Application Publication No. US 2019/0110687, which is incorporated herein by reference.

As another illustrative example, a single or multiple tunable QCL can be used as the illuminator 108 with an appropriate photodetector element or photodetector array of pixels used as the response detector 110. For example, a practical 4 QCL system can provide IR illumination wavelengths between 820 $cm^{-1}$ and 1680 $cm^{-1}$, such as with available incremental wavenumber steps being similar to those from an FTIR probe, for example. In another practical example 32 QCLs can be integrated onto a single QCL chip, with an individual one of the 32 QCLs having a 160 $cm^{-1}$ range tunable in 5 $cm^{-1}$ steps, with the individual QCL ranges being specifiable to be overlapping, non-overlapping, or partially overlapping to obtain the desired IR spectral range and, if desired, to permit some redundancy in allowing different QCLs to be tuned to the same wavelength. Again, for the QCL approach, the full spectral resolution or a specified subset of which can be used for training the learning model 118. By appropriate training, the trained learning model 118 can employ reduced set of wavelengths at run-time for multi-dimensional tissue classification. By appropriate training, this reduced set of wavelengths used at run-time for multidimensional tissue classification using the trained model 118 can be selected to fall within the output range of a single tunable QCL, such that only a single tunable QCL need be tuned and used at run-time for performing the multidimensional tissue classification using the trained model 118.

At 204, regardless of (or depending upon) which technique is to be used for analyzing the spectral data acquired from the response detector 110, it be desirable to first apply one or more pre-processing techniques to the acquired spectral data. Examples of such spectral techniques can include baseline adjustment, filtering, or the like. One particularly useful pre-processing technique can include applying a second derivative to the acquired spectral data, such as using a specified spectral resolution of applying the second derivative (e.g., skipping a specified number of wavenumbers), such as to help reduce, attenuate, or eliminate an effect of gaseous water vapor otherwise present in the spectral data. An illustrative example and more detailed explanation of applying such a second derivative technique is described in more detail elsewhere in this document.

It is possible to develop one or more metrics for use in analyzing the spectral response data from the response detector 110 for training the learning model 118. For example, such metrics can include one or more or ratios of peak absorbances, calibrant dot product scores, tissue scattering metrics, baseline correction metrics, or the like.

At 206, the pre-processed spectral data from the training data set can be used to train the learning model 118, such as by using artificial intelligence or machine learning techniques for training the learning model 118, such as to obtain a useful reduced set of wavelengths for use at runtime for classifying tissue into tumor and non-tumor categories—as well as into one or more of a variety of other useful diagnostic categories, such as described herein. One example of such a machine learning technique can be referred to as a Support Vector Machines (SVM) learning technique, which can be used to select a reduced wavelength set for run-time tissue discrimination using the trained model 118.

At 206, the training can include using machine learning support-vector machines (SVMs) which are supervised programs using a training data set to obtain an optimized separating surface between different groups such as for tissue classification. While these different classification groups can be limited to two groups (e.g., tumor tissue classification group and non-tumor-tissue classification group), the present techniques can also be adapted to classification according to more than two-groups, such as in a complex multi-dimensional space. As explained herein, SVM can be used to develop decision equation values representing hyperdimensional distances from the optimized separating surface. SVMs can provide robust prediction methods. After sufficient training of the learning model 118, resulting decision equations of the trained learning model 118 can be used at run-time to test new tissue specimen spectral data, such as in a clinical or other diagnostic setting. As explained herein, SVM can be used to efficiently perform classification such as by implicitly mapping their inputs into one or more high-dimensional feature spaces. The resulting linear SVM trained learning model 118 using the kernel trick can be more efficient and accurate for tissue classification, particularly in use cases in which tissue classification into more than two groups is desired. It can also be more robust, such as compared to non-linear SVM, in that it can be better adapted to new tissue specimens and can be less susceptible to perturbations or noise, which might otherwise be magnified or otherwise corrupt the diagnostic ability when using a non-linear SVM approach. Nonetheless, non-linear SVM techniques, such as using radial basis functions, or other artificial intelligence or machine learning techniques can be used.

At 208, the trained learning model 118 can be used at run-time to perform tissue classification of one or more further tissue specimens 102, such as in a diagnostic or clinical setting, such as during a diagnostic or treatment procedure being performed on a patient, such as described herein.

At 210, one or more indications of a result of the tissue classification can be provided to a diagnostician, clinician, or other user, such as described herein.

At 212, the one or more indications of the result of tissue classification can optionally be provided as an RGB or other displayed image provided to the user, such as by mapping at least two—or more than two—tissue classifications to a color coding schema to be provided on the display to the user, such as described herein.

B. Training Example Using SVM

B.1 Model Representation Example

This section provides an example of training the learning model 118, such as using linear SVM. Such training of the learning model 118 can involve extracting cancer and different cell-type decision equations, such as from a training set that can include a library of full-range infrared (IR) response spectral data from tissue section specimens 102. SVM decision equations can be used to determine an optimal hypersurface, such as for separating measurements into two groups, like tumor and non-tumor, or more than two groups, which can help provide additional diagnostic support capability. The trained learning model 118 can yield a down-selected set of spectral response wavelengths, such as can help provide quick, accurate, and efficient run-time analysis of other tissue specimens 102. This can permit detecting tumors or one or more other tissue cell-structural characteristics at run-time, such as using an IR spectroscopy probe or other system for illuminating and analyzing a response from such other tissue specimens 102, such as in a diagnostic or clinical setting.

In an example, the SVM decision equations can be determined using a fuller-range and fuller-resolution mid-infrared electromagnetic energy spectrum, such as useful for spectroscopic tissue characterization. The SVM decision equations can be efficiently stored in the learning model 118 such as to represent the SVM output as three IR spectra and a constant. More particularly, such a representation can include: (1) an SVM $\beta$ spectrum; (2) an average (or other central tendency) of the training spectra; (3) a standard deviation (or other spread) of the training spectra; and (4) a bias or offset constant.

The techniques described can allow SVM decision equation values to be determined without requiring training software and without requiring output of all of the support vectors-which may otherwise number in the hundreds for a tissue characterization use-case, with each such support vector being a full IR spectrum. The compact model representation allows efficient training and efficient run-time tissue classification. This can be very helpful, in practice. For example, it can help enable expanding the diagnostic information provided to a clinician or other user to include more variety in tissue classification information-such tissue classification information need not be limited to the two categories of tumor and non-tumor.

This document also describes practical examples, such as using two IR imaging data sets of tissue specimens 102 with tumors, e.g., SKH1 mouse with skin cancer and colorectal cancer metastatic to the liver in a human. This document describes determining and using the SVM $\beta$ spectrum, such as for recognizing and classifying tumors. This document also explains examples of how average IR spectra of tissue groups (like tumor and nontumor, or other tissue groups) can employ the SVM $\beta$ spectrum, such as to obtain group decision spectra that can help reveal and select the most useful spectral wavelengths in making the decision, such as for training the learning model 118 to be used at run-time with a reduced set of the most useful spectral wavelengths in efficiently classifying other tissue specimens 102, such as using mid-IR spectroscopy.

The present techniques of using SVM can offer certain advantages over other machine learning techniques, such as in extracting results and usability without requiring training software. However, certain aspects of the present disclosure can be used with non-SVM machine learning, if desired. This section describes developing the relation of SVM decision equations to full, unscaled training data spectra. An "SVM $\beta$ spectrum" can be defined. The SVM $\beta$ spectrum can include the form of an IR spectrum, but, advantageously, can include the summed response of all support vectors at each spectral training wavelength. The SVM $\beta$ spectrum can efficiently and conveniently be used for tissue classification, such as to determine "group decision spectra", such as which can be efficiently and accurately used to classify tissue, such as into two groups, or into more than two groups, such as along various different dimensions of interest to a diagnostician or clinician.

The present SVM techniques can be used for training the learning model 118, such as to determine an optimal hypersurface such as for separating measurements of different groups (such as for tissue classification of tumor and nontumor groups). The SVM techniques can include selecting training data referred to as "support vectors" that lie between the two identified groups of interest. When training the learning model 118 using full range and full resolution IR response spectra as the training data set, the support vectors can have the form of full-range and full-resolution digitized IR response spectra. Using a linear kernel function and spectral scaling, the linear SVM decision equation can be represented, for a full IR response spectrum to be tested, $Test_{k,j}$, as $$d_k = b + \sum_i \alpha_i y_i \left\langle \frac{SV_{i,j} - \overline{Train_j}}{\sigma_{Train_j}} \middle| \frac{Test_{k,j} - \overline{Train_j}}{\sigma_{Train_j}} \right\rangle \quad (1)$$

In Equation 1, the three indices are i for the support vectors, j for the spectral steps (e.g., the dot product index), and k for the response spectrum to be tested for training the learning model 118. The scalar offset or bias is b, $a_i$ are the weights of the support vectors chosen to be near the separating hypersurface, and $y_i$ is the group membership (e.g., nontumor or tumor, in an illustrative example). The linear kernel is represented in brackets in Equation 1, and contains the support vectors, $SV_{i,j}$, and the test spectrum, $Test_{k,j}$, which can be scaled, such as with respect to the mean or other central tendency of the training set, $\overline{Train_j}$, and with respect to the standard deviation or other spread of the training set, $\sigma_{Train_j}$.

The decision equation value, $d_k$ can represent the perpendicular distance from the separating hyperplane to a test spectrum as a decision data point. Values of $d_k > 0$ classify into a one group, and $d_k < 0$ classify into the other. In order to use the decision equations in this form, however, the spectral data file of every support vector needs to be transmitted to the potential user, and there can easily be hundreds of support vectors, with each such support vector including a full IR response spectrum from a tissue specimen of the training data set.

The present inventors have recognized that a more useable form can be determined, such as via algebraic manipulation of Equation 1. First, the support vector summation can be moved into the bracket or vector inner product. Then, commuting the row and column of the inner product, the decision equation can be written as $$d_k = b + \left\langle \frac{Test_{k,j} - \overline{Train_j}}{\sigma_{Train_j}} \middle| \beta_j \right\rangle, \text{ where} \quad (2)$$

$$\beta_j = \sum_i \alpha_i y_i \left( \frac{SV_{i,j} - \overline{Train_j}}{\sigma_{Train_j}} \right),$$

in which $\beta_j$ has the form of an IR spectrum when using the full set of spectral steps, within the spectral range of interest, for training. The term $\beta_j$ is referred to herein as the "SVM β spectrum". Thus, as represented in Equation 2, the trained learning model 118 can be represented using a trained model representation that includes at least: (1) a β spectrum including the fuller wavelength set; (2) a central tendency indicator (μ) of the training set; (3) a spread indicator (σ) of the training set; and (4) a scaling factor.

A benefit a model representation such as shown in Equation 2 is that subsequent use of this form of decision equation only involves representing three spectra: (1) the average (or other central tendency) of the training set ($\overline{Train_j}$), (2) the standard deviation (or other spread) of the training set ($\sigma_{Train_j}$), and (3) the $\beta_j$ or SVM β spectrum. In addition to these three spectra, this form of the decision equation can include the scalar bias constant, b. As represented in Equation 2, the SVM β spectrum includes contributions from all of the support vectors at each spectral step within the range of spectral wavelengths of the training response spectral data set. Therefore, the SVM β spectrum can be studied and used for insight into which particular wavelengths are most significant in making successful decisions with regard to group classification of tissue specimens. The SVM β spectrum form of one spectrum is much more convenient and efficient to store, represent, and to convey to users than the whole set of spectral support vectors, which could number in the hundreds for a tissue classification use case.

Decisions, based on the $d_k$ variable of Equations 1 and 2, constitute classifications of spectral data into one of the two different groups. However, a spectral analysis can be useful and desired in certain applications. For the following discussion, let values of $d_k > 0$ classify into the "+ group" and $d_k < 0$ classify into the "−group", which can represent tumor and nontumor groups (or other tissue classification groups), respectively. Then the $\beta_j$ spectrum can be divided into two spectra in which:

$$\beta_j^+ = \begin{cases} \beta_j & \text{if } \beta_j > 0 \\ 0 & \text{if } \beta_j \leq 0 \end{cases} \text{ and } \beta_j^- = \begin{cases} 0 & \text{if } \beta_j > 0 \\ \beta_j & \text{if } \beta_j \leq 0 \end{cases}, \quad (3)$$

As represented in Equation 3, negatives values of $\beta_j$ can be replaced by zeros in, $\beta_j^+$ and positive values of $\beta_j$ can be replaced by zeros in $\beta_j^-$. Given IR spectra of the two groups, $G_j^+$ and $G_j^-$, then the contribution of each spectral wavelength to the decision, that is, the group decision spectrum, $Td_j^+$ or $Td_j^-$, can be represented as:

$$Td_j^\pm = \frac{b}{j_{max}} + \left( \frac{G_j^\pm - \overline{Train_j}}{\sigma_{Train_j}} \right) \beta_j^\pm, \quad (4)$$

In Equation 4, $j_{max}$ is the number of digital spectral steps within the fuller spectral wavelength range of interest for training the learning model 118. Plots of the group decision spectra, $Td_j^+$ or $Td_j^-$, can reveal the most significant wavelengths for making tissue classification decisions about the "+" or "−" groups.

Given this explanation, the below Experimental section description provides an illustrative example of acquisition of IR spectral training data sets on frozen tissue section specimens, such as with several tumors. The below Results section description illustrates an example of determining the IR spectra such as for the tumor and nontumor groups (or any other groups, as desired), $G_j^+$ and $G_j^-$, and the initial SVM analysis. The Results section continues with a description of extracting the SVM β spectra and the group decision spectra, $Td_j^+$ or $Td_j^-$. As explained below, while the mouse tissue specimen data involved all of the data for training, only a fraction of the human metastatic liver cancer data set was used for training the model 118 into four different training groups (e.g., tumor tissue category, nontumor tissue category, lymphocyte-rich tissue category, and blood-rich tissue category). The Results section also describes using multi-SVM decision equations for imaging test data, such as for displaying diagnostic data to a user, as well as describing extracting multigroup SVM β spectra.

B.2 Experimental Example—Mouse Model for Squamous Cell Carcinoma

Figures 3A, 3B:
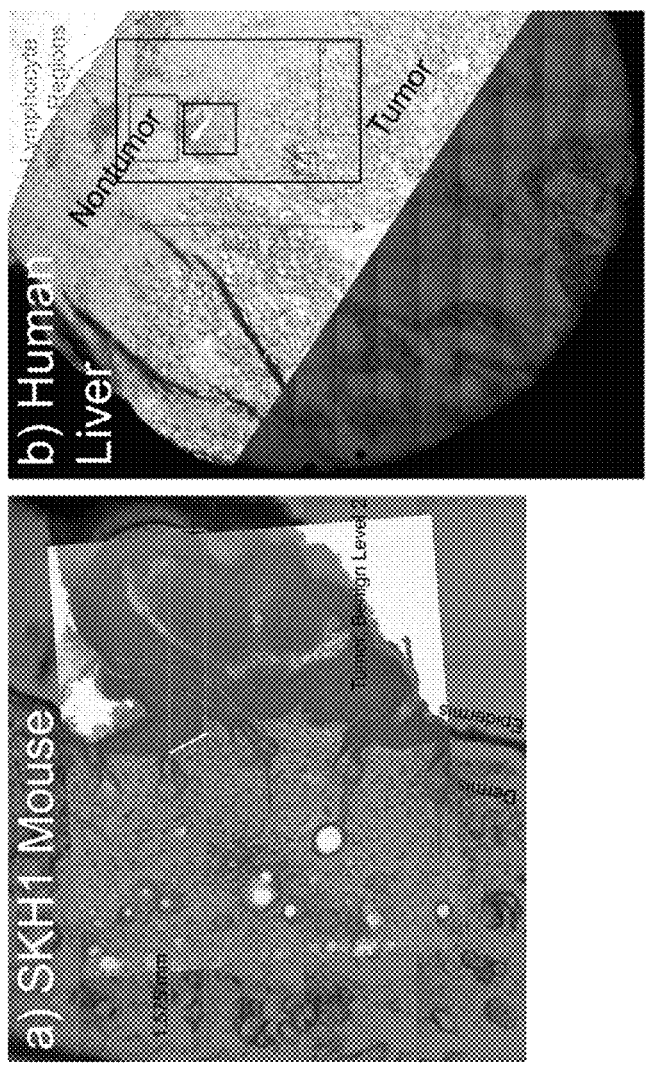
FIG. 3A shows a microscopy image of a frozen mouse tissue section specimen, including an area scanned with FTIR imaging spectroscopy, and overlaid in registry with information from a later H&E stain.
FIG. 3B shows an example of a microscopy image of a frozen tissue sample section of colorectal cancer metastatic to the liver, showing tumor and non-tumor and lymphocyte-rich and blood-dominated regions.

FIG. 3A shows a microscopy image of a frozen mouse tissue section specimen from an SKH1 mouse tumor, which is shown in FIG. 3A at right, extending out from the epidermis. The area defined by the rectangular red box shown in FIG. 3A was scanned with FTIR imaging spectroscopy. The white line in FIG. 3A divides tumor and nontumor regions. After acquiring the FTIR imaging spectroscopic data, the same tissue specimen was treated with a hematoxylin-and-eosin (H&E) stain, which has been overlaid in registry in FIG. 3A.

The SKH-1 mouse model of UV-induced cutaneous squamous cell carcinoma (SCC) closely recapitulates the human disease. The largest tumor was removed, snap frozen, and a 3 μm thick section with no fixation or paraffin embedding was mounted on a ZnSe IR window, shown as yellow in FIG. 3A. In FIG. 3A, the inside of the mouse is to the left and the epidermis or outer layer of skin would have been vertically down the center if not for a tumor growing out of the epidermis toward the center right of FIG. 3A.

The 1.575 mm×0.100 mm area marked by the red rectangle in FIG. 3A was subjected to FTIR hyperspectral microimaging in the mid-IR range. The region of study was divided into 252×16 units or 4032 square pixels each with 6.25 μm square edges. An FTIR spectrum was recorded at each of the 4032 pixels (750-4000 cm$^{-1}$ spectral range, 16 scans per pixel). After the hyperspectral imaging, the exact same tissue specimen in the same sample holder was stained with H&E and imaged with a different optical microscope. In FIG. 3A, the result has been overlaid in registry with the yellowish pre-IR imaging picture with scaling and a slight counterclockwise rotation. Note that the H&E image had a ZnSe yellow color cast, from the ZnSe IR windows, which was removed and then contrast-adjusted. The epidermis stained dark red with H&E, like the tumor, and was punctuated with hair follicles down the center of FIG. 3A. The dermis was riddled with vesicles and stained a lighter red/pink color. In FIG. 3A, the dark red (right) to light red (left) transition of the H&E stain image clearly delineates the tumor edge, which has been indicated in FIG. 3A with an overlaid white line. Pixels to the right of the white line were indexed as tumor group, while pixels to the left were indexed as nontumor group. The clear assignment of tumor and nontumor regions yielded a useful data set for extracting an SVM β spectrum and group decision spectra.

B.3 Experimental Example—Colorectal Cancer Metastatic to the Liver

FIG. 3B shows an example of a microscopy image of a frozen tissue sample section of colorectal cancer metastatic to the liver. In FIG. 3B, the tumor is at the bottom, nontumor regions at the top, and purplish regions are rich in lymphocytes. The area in the larger black rectangle was scanned with FTIR imaging spectroscopy and the green box in FIG. 3B represents a nontumor region and the red box represents a tumor region. The smaller black box is rich in lymphocytes, while the orange box is blood dominated, in FIG. 3B.

The tissue sample in FIG. 3B was snap frozen in liquid nitrogen without formalin fixation or dehydration and a cryostat section of ~3 μm thickness was obtained at −20° C. This section contains lipid, water, and less perturbed proteins than fixed samples. The 2.200 mm×0.300 mm area marked by the larger black rectangle in 3B contained 352×192=67,584 pixels. An FTIR-acquired spectrum was recorded at each pixel using an array detector having 4 cm$^{-1}$ resolution, 750-4000 cm$^{-1}$ range, 16 scans per pixel, 6.25 μm square pixel edge, with 4 adjacent windows. An H&E stain was performed immediately on the exact same tissue sample after the IR imaging was completed. The yellow color cast of the ZnSe optics was removed from the optical microscope H&E stain image, contrast-adjusted, scaled, rotated and overlaid with the IR image in FIG. 3B. The H&E stain allowed the pathologists training a learning model, such as the model 118, to assign the red, black, green, and orange rectangles within the scanning box as for tumor, lymphocyte rich, nontumor, and blood-rich regions, respectively. These assignments by the pathologists provided ground truth data allowing SVM beta spectra and group decision spectra to be determined.

B.4 Results

Figure 4B:
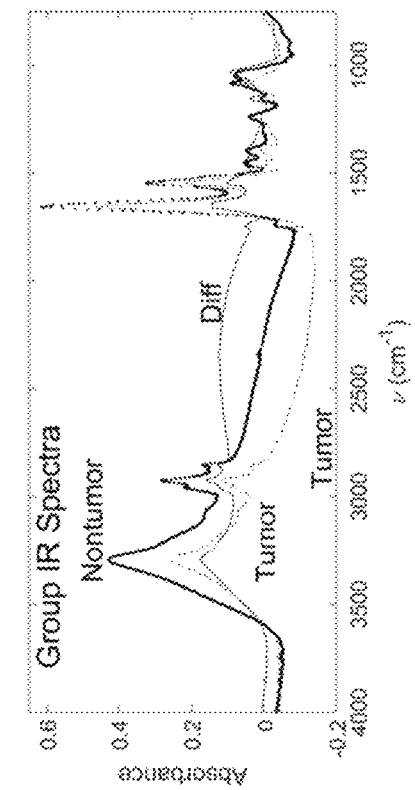
FIG. 4B is an example of an IR spectral response graph of absorbance vs. frequency for metastatic human liver cancer group IR spectra, showing tumor in red, non-tumor in green, and the difference in black.
Figure 4D:
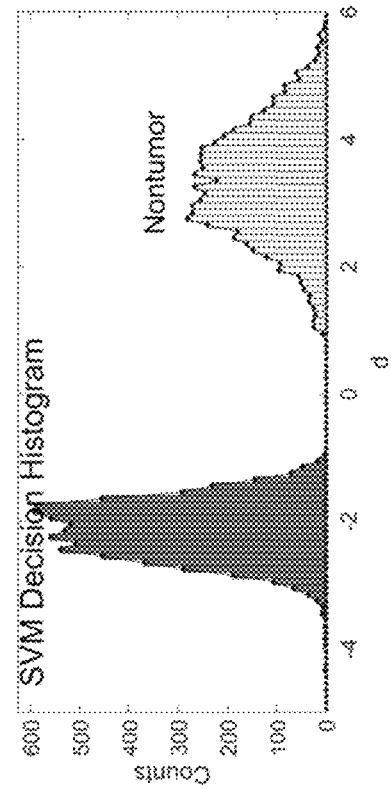
FIG. 4D is an example of an SVM decision histogram (counts vs. d-value) for the metastatic human liver cancer data shown in FIG. 4B, with non-tumor classification shown in green and tumor classification shown in red.
Figure 4A:
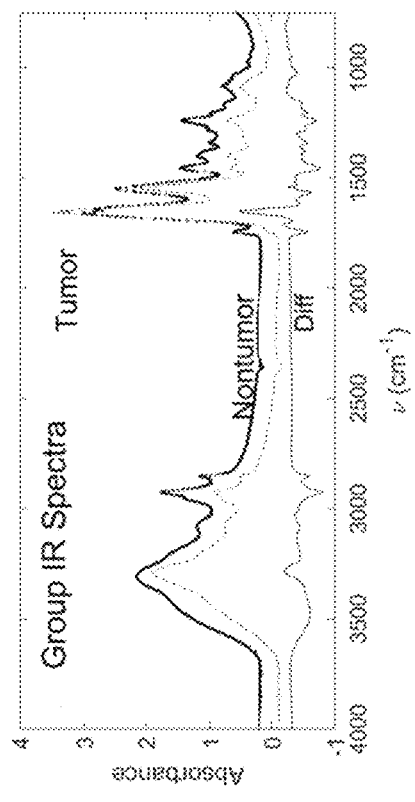
FIG. 4A is an example of an IR spectral response graph of absorbance vs. frequency for SKH1 mouse tumor group IR spectra, showing tumor in red, non-tumor in green, and the difference in black.

FIG. 4A is an example of an IR spectral response graph of absorbance vs. frequency for SKH1 mouse tumor group IR spectra, showing tumor in red, non-tumor in green, and the difference in black.

FIG. 4B is an example of an IR spectral response graph of absorbance vs. frequency for metastatic human liver cancer group IR spectra, showing tumor in red, non-tumor in green, and the difference in black.

Figure 4C:
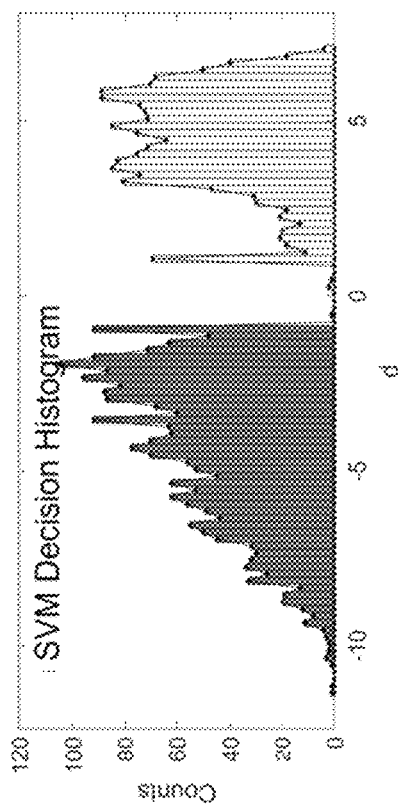
FIG. 4C is an example of an SVM decision histogram (counts vs. d-value) for the mouse data shown in FIG. 4A, with non-tumor classification shown in green and tumor classification shown in red.

FIG. 4C is an example of an SVM decision histogram (counts vs. d-value) for the mouse data shown in FIG. 4A, with non-tumor classification shown in green and tumor classification shown in red.

FIG. 4D is an example of an SVM decision histogram (counts vs. d-value) for metastatic human liver cancer shown in FIG. 4B, with non-tumor classification shown in green and tumor classification shown in red.

The mouse tissue section of FIG. 4A had a clearly indicated transition from tumor to nontumor (white line in FIG. 3A). FIG. 4A shows an example of the IR spectra of the tumor (red) and nontumor (green) regions on a per pixel basis. These spectra represent the $G_j^+$ and $G_j^-$ spectra useful for Equation 4. The absolute intensities are meaningful (they are on a per pixel basis) with this result and there are definitive differences between the tumor and nontumor regions as highlighted by the black trace, which is the difference spectrum. To help obtain the best signal-to-noise ratio on the SVM β spectrum, all of the training data set library of 4032 IR spectra were used as the training set. With clear indexing for tumor and nontumor groups, SVM was performed with a linear kernel and scaling, such as described herein, producing zero classification errors. The array of decision equation values, $d_k$ of Equations 1 or 2, was plotted as a histogram with 0.2 unit bins in FIG. 4C (bottom left) using red for tumor and green for nontumor. The big gap between bins containing the −1 and +1 decision values and the small number of counts within the −1 and +1 gap indicates an excellent modeling of the training set data by the linear SVM model 118. Also, the nature of the histogram outside of the gap is interesting.

Figure 5A:
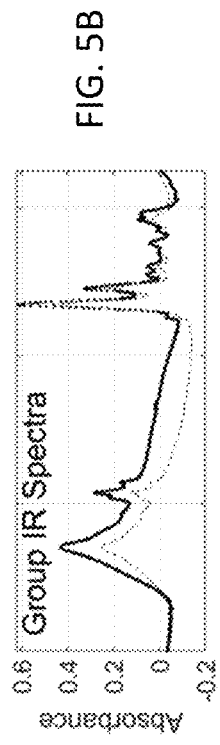
FIGS. 5A, 5C, and 5E respectively show examples, from the SKH1 mouse data, of the group IR spectra (FIG. 5A), a representation of $G_j^+$ or $G_j^-$, the SVM spectrum from Equation 2 (FIG. 5B), and a representation of the group decision spectra, $Td_j^+$ or $Td_j^-$ of Equation 4 (FIG. 5E).
Figure 5C:
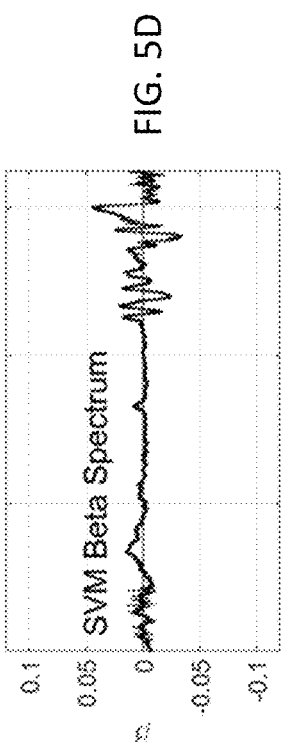
Figure 5E:
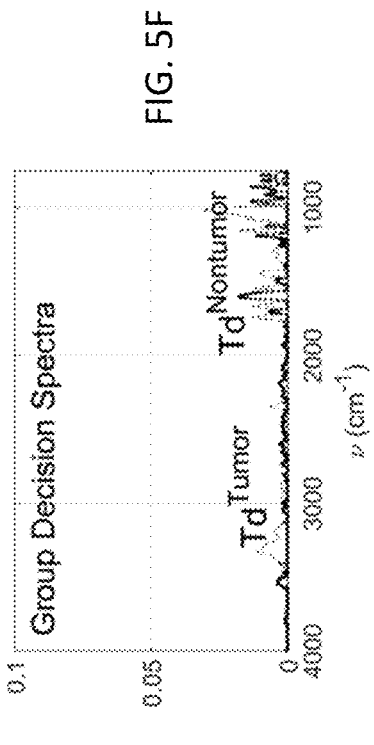

FIGS. 5A, 5C, and 5E respectively show examples, from the SKH1 mouse data, of the group IR spectra (FIG. 5A), a representation of $G_j^+$ or $G_j^-$, the SVM β spectrum from Equation 2 (FIG. 5B), and a representation of the group decision spectra, $Td_j^+$ or $Td_j^-$ of Equation 4 (FIG. 5E), respectively. Since the spectral region from 1950-2500 $cm^{-1}$ is largely devoid of fundamental vibration features (with avoidance of $CO_2(g)$ at ~2350 $cm^{-1}$), this region of the SVM β spectrum shows a standard deviation of 0.050, specifying the noise level (shown by the blue trace in FIG. 5C) of the determination when the big signals are about 0.4. The SVM β spectrum of FIG. 5C was smoothed with a Savitsky-Golay procedure spanning 20 steps with a $2^{nd}$ order polynomial (cyan trace in FIG. 5C). Smoothing reduces the pure noise region by 48% while signal in the amide I protein band (1654 $cm^{-1}$) is only reduced by 310%. The group decision spectra displayed in FIG. 5E are from the smoothed SVM β spectrum (cyan) rather than the original (blue), to help benefit from reduced noise.

Figure 5B:
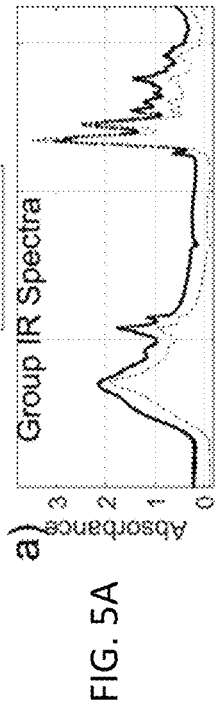
FIGS. 5B, 5D, and 5F respectively show examples, from the metastatic human liver cancer data, of the group IR spectra (FIG. 5B), a representation of $G_j^+$ or $G_j^-$, the SVM β spectrum from Equation 2 (FIG. 5C), and a representation of the group decision spectra, $Td_j^+$ or $Td_j^-$ of Equation 4 (FIG. 5F), respectively.
Figure 5D:
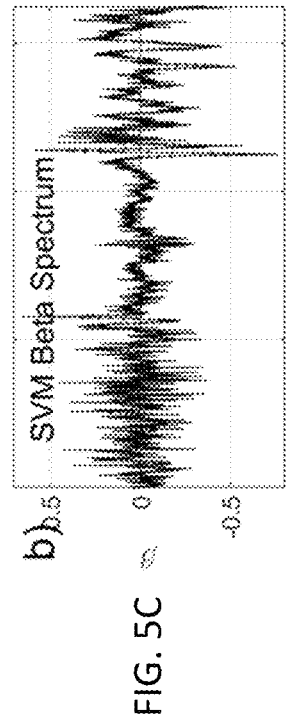
Figure 5F:
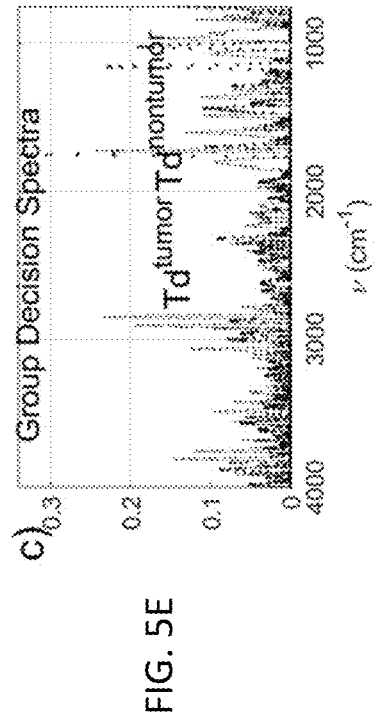

Considering that the full IR spectrum provides a response at 1626 wavenumbers and produces zero SVM prediction errors, it is helpful to determine how much of the full IR spectrum is useful to obtain a reasonable cancer decision. Reducing the full spectral data set to only include the spectral response at the top five tumor and top five nontumor wavenumbers, the linear SVM analysis makes 70 errors which is 1.74% wrong. Thus, even if the model were limited to the top 10 wavenumbers, using the trained model at run-time tuned to only those selected top 10 wavenumbers would still result in making more than 98% of the decisions correctly. FIGS. 5B, 5D, and 5F respectively show examples, from the metastatic human liver cancer data, of the group IR spectra (FIG. 5B), a representation of $G_j^+$ or $G_j^-$, the SVM β spectrum from Equation 2 (FIG. 5C), and a representation of the group decision spectra, $Td_j^+$ or $Td_j^-$ of Equation 4 (FIG. 5F), respectively. There will always be regions where the pathologist training the model is uncertain, or instances where both tumor and nontumor tissues coexist at the same location, so a strategy can be employed to define regions in which all of the training pathologists were in agreement as to the identity of the tissue. There were 7236, 5467, 6324, and 1271 pixels in the tumor, lymphocyte-rich, nontumor, and blood-rich regions as defined with boxes in FIG. 3B. The average IR spectrum for tumor and nontumor training groups, i.e. the $G_j^+$ and $G_j^-$ spectra useful for Equation 4, are shown in FIG. 4B. The lymphocyte-rich and blood-rich groups will be further explained elsewhere in this document. The histogram of decision equation values for nontumor vs tumor is given in FIG. 4D and reveals no errors from the training set. Also, the distributions of both tumor and nontumor are pushed further away from the dividing line than in the case of the SKH1 mouse data, so this is an excellent training data set for extracting the SVM β spectrum, which is shown in FIG. 5D (blue trace). The cyan curve in FIG. 5D is smoothed with a Savitsky-Golay procedure spanning 20 steps with a $2^{nd}$ order polynomial. Again, the spectral region from 1950-2500 $cm^{-1}$ (avoiding $CO_2(g)$) defines the noise of the SVM β spectrum as a standard deviation of 0.0007 from the blue trace of FIG. 5D, which is small compared to the biggest signals of ~0.04. FIG. 5F shows an example of the group decision spectra, $Td_j^+$ or $Td_j^-$ of Equation 4 using the smoothed SVM β spectrum (cyan trace of FIG. 5D). Significant differences between the SKH1 mouse skin cancer and the human metastatic liver cancer SVM β spectra can be noted, as well as differences in the group decision spectra which reveal the most useful wavelengths for use in the model for efficient and accurate run-time tissue classification using the trained model 118.

C. Tissue Classification into More than Two Groups and Decision Equation Imaging Results Such as for Display to a User SVM is most useful when there are only two groups to choose from, such as tumor and nontumor. For example, definitive results showing an effectively trained model were obtained from the SKH1 mouse tumor data, but all of the training set data (a library of 4032 IR spectra) was used for the training to help get the best signal-to-noise ratio on the SVM β spectrum.

Nonetheless, practical situations can involve more than two groups. The training data set described herein for the case of colorectal cancer differs in that not all of the data was used for training. FIG. 3B shows regions rich in lymphocytes (purplish regions, small black box, 5467 pixels) and regions rich in blood (orange box, 1271 pixels), in addition to the tumor (red box, 7236 pixels) and nontumor (green box, 6324) regions. In a further training example, decision equations were trained for each of these four groups against the other three, thus employing a one-vs-the-rest multiclass SVM classification strategy.

Figure 6A:
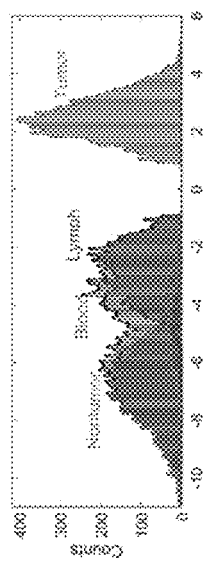
FIGS. 6A, 6B, 6C, and 6D show examples of histograms of one-vs-the-rest multiclass SVM classifications in metastatic human liver cancer.
Figure 6B:
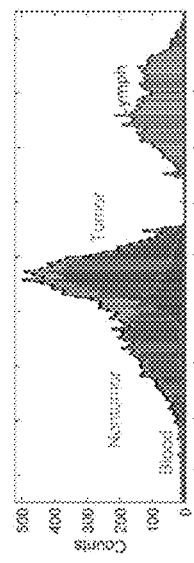
Figure 6C:
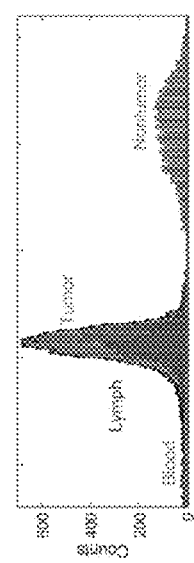
Figure 6D:
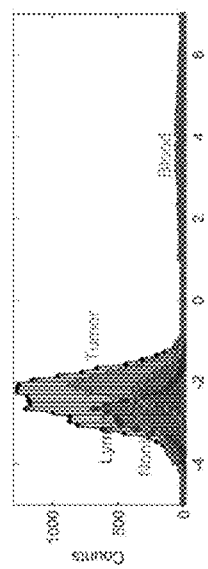

FIGS. 6A, 6B, 6C, and 6D show examples of histograms of one-vs-the-rest multiclass SVM classifications in metastatic human liver cancer. Histograms of the decision equation values for each one of the four groups against the rest of the four groups are shown in FIG. 6A (tumor vs. nontumor, blood, and lymph), 6B (lymph vs. tumor, non-tumor, and blood), 6C (non-tumor vs. tumor, blood, and lymph), and 6D (blood vs. tumor, non-tumor, and lymph). Note that only one classification error out of 20,298 training pixels was made while training the four decision equations using the linear SVM techniques described herein.

An imaging technique was developed based on the 4 decision equations used for classifying the four different groups. A decision equation value was calculated for each particular group of the four groups at each of the 67,584 pixels in the full metastatic liver set. A scaling scheme set all negative values to zero and all positive values were divided by the maximum decision equation value, thereby producing values between zero and one. The scaled tumor result values were used in an RGB coloring scheme in which tumor tissue was represented by the color red, nontumor tissue was represented by the color green, lymphocyte-rich tissue was represented by the color blue, and the blood rich tissue were represented by the color yellow (equal amounts were placed in the red and green RGB values in the RGB image).

FIG. 7B shows the resulting RGB image, which is shown side-by-side with the H&E stain image shown in FIG. 7A. The RGB image of FIG. 7B shows an example of an image that can be displayed to a diagnostician or clinician, such as on the display 122, such as to provide a color visual representation of diagnostic information that can include information about more than two groups of tissue classifications. Considering that only 30% of the available training IR spectral data was used for training, it can be observed in FIG. 7B that there is very little overlap of the red, green, blue, and yellow colors for the 70% of the available training data (outside the boxed regions) that was not used in training, but instead used for tissue classification based on the more limited training data set. In FIG. 7B, the test regions not used in training the model 118 are in excellent agreement with the H&E stain in FIG. 7A. Such decision equation imaging (e.g., and encoding results into a useful diagnostic color scheme) can help reveal interesting textures in the tissue groups-which are different than that what is revealed by H&E staining of FIG. 7A. Simply put, there is information in the actual numerical value of the decision equation results beyond their application in classifying the tissue into a particular group. This aspect is also revealed by the histograms for one-vs-the-rest multiclass SVM classification in FIGS. 6A, 6B, 6C, and 6D. In each case there are three groups taken together ("rest") for the SVM classification decision, but histograms corresponding to the different "rest of" groups have been plotted as separate distributions in FIGS. 6A, 6B, 6C, and 6D, showing distinct differences among the different groups included into the "rest of" (left-hand side of each histogram in FIGS. 6A, 6B, 6C, and 6D) be distinguished from a particular one group.

D. SVM Reduction of Wavelengths

While a reduced set of particularly useful wavelengths for tissue classification can be chosen, it is also possible to systematically remove a fraction of the wavelengths, e.g., iteratively, while assessing the corresponding resulting classification error rate of using each reduced wavelength set with linear SVM. Doing so can determine how much spectral information can be removed without compromising the decisions, so that the resulting trained model using a reduced wavelength set can be efficiently and accurately used at run-time by tuning the system to only illuminate and observe responses at the selected reduced set of wavelengths, thereby saving time, enabling more rich information to be gathered and provided to the user, or both.

Figure 8A:
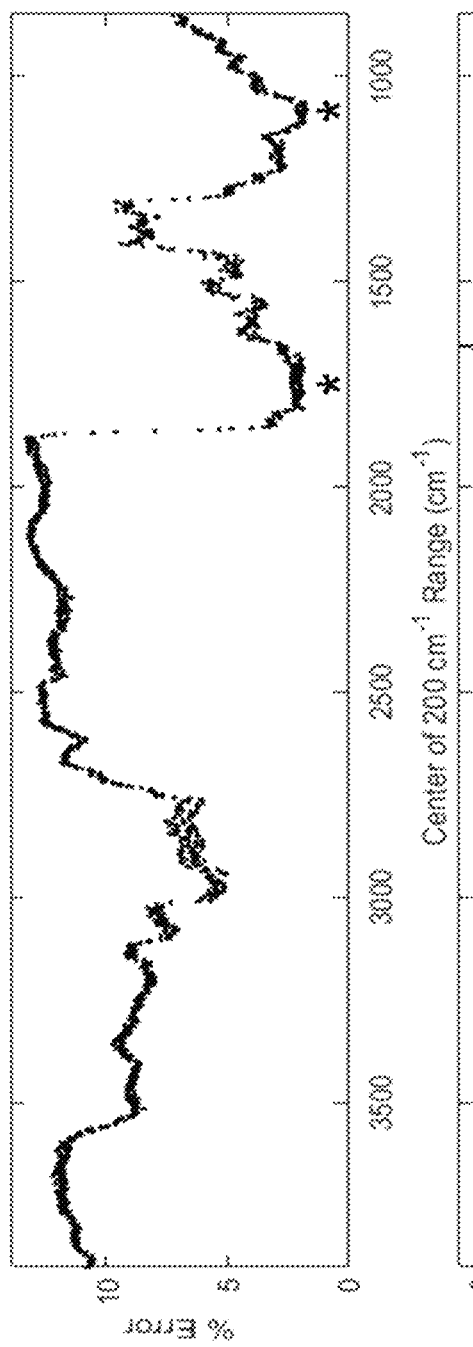
FIGS. 8A, 8B shows examples of reducing wavelength range data, including by scanning along a limited range of a wider range, such as to help determine which portions of the wider range are most useful for tissue classification.
Figure 8B:
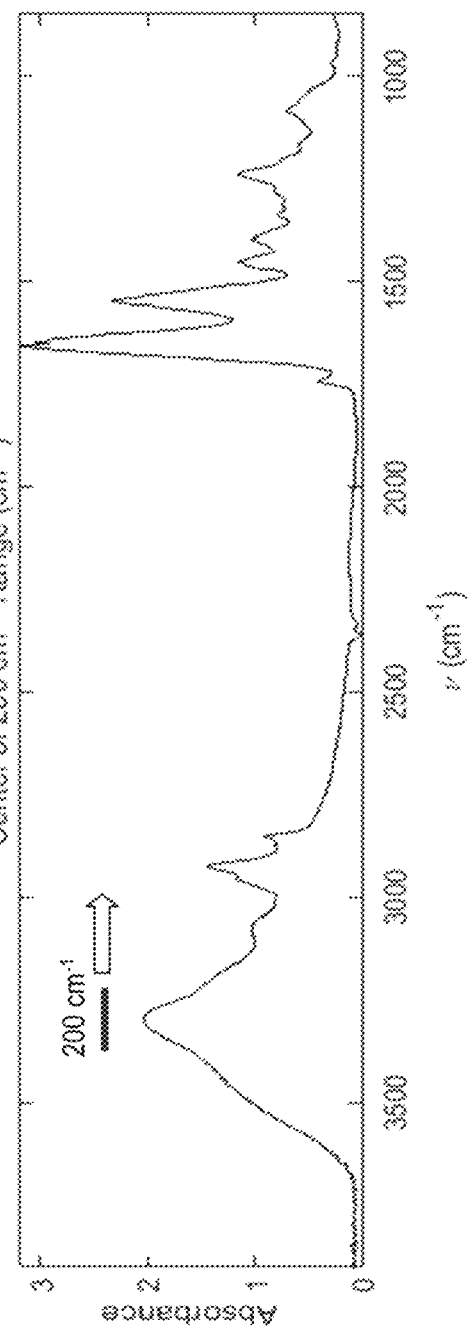

FIGS. 9A-9G show spectral absorbance vs. frequency data, with corresponding decision histogram data shown in FIGS. 10A-10G, as wavelengths are reduced from 1626 wavelengths (FIG. 9A, FIG. 10A), to 813 wavelengths (FIG. 9B, FIG. 10B), 407 wavelengths (FIG. 9C, FIG. 10C), 204 wavelengths (FIG. 9D, FIG. 10D), 102 wavelengths (FIG. 9E, FIG. 10E), 51 wavelengths (FIG. 9F, FIG. 10F), and 26 wavelengths (FIG. 9G, FIG. 10G). The mouse tumor data were used for this purpose, starting with all of the wavelengths (1626 steps of 2 $cm^{-1}$ each in the range from 750-4000 $cm^{-1}$). Data were removed in two systematic ways: (1) by taking data within only a 200 $cm^{-1}$ range and scanning that range across the full spectrum (FIG. 8B shows the full spectrum and a 200 $cm^{-1}$ range; FIG. 8A shows the error as the range is scanned across the full spectrum); and (2) by only using data selected at increasing intervals which effectively cut the number of wavelengths used in half at each successive stage (see FIGS. 9A-9G and FIGS. 10A-10G). Each set of reduced data was evaluated with the linear SVM model described herein, yielding an error measurement of the sum of wrong tumor and nontumor predictions for comparison. The best 200 $cm^{-1}$ regions are indicated with asterisks in FIG. 8A. These include a set of wavelengths centered from 1680-1810 $cm^{-1}$ with ~2% error including the ester linked lipid band and the amide I protein band, as well as a set centered from 1120-1060 $cm^{-1}$ including a band centered at 1085 $cm^{-1}$ with 1.7% error. This is a region with spectral information bands carrying information for glycogen, phosphate-containing molecules, and many others.

The effect of using a full spectral wavelength range, but selecting data with increasing intervals in between wavelengths used (effectively cutting the number of wavelengths used in half at each successive stage) is illustrated in FIGS. 9A-9G and the corresponding FIGS. 10A-10G. The original data is shown at the top left, in FIG. 9A, with 1626 steps spaced by 2 $cm^{-1}$ each, while the last at the bottom left (FIG. 9G) has only 26 steps of 128 $cm^{-1}$ each. The corresponding decision equation histograms using a total of 13,560 pixels in the tumor and nontumor training groups are shown in FIGS. 10A-10G on the right with the corresponding percent error listed at the far right of each of FIGS. 10A-10G.

The original data (FIG. 9A, FIG. 10A) has 0% error and the trend ends with 5.26% error in FIGS. 9G, 10G. It can be noted that the filling of the region of d=−1 to +1 (indicated with light blue vertical lines in FIGS. 10A-10G) increases as the number of employed wavelengths decreases. Thus, FIGS. 10A-10G exhibit the reduced effectiveness of the decision mechanism as more and more spectral information is removed. Even so, the resulting model can remain effective and robust at certain levels. For example, because the use of only 51 wavelengths at 4 $cm^{-1}$ resolution across the full spectrum at a spacing of 64 $cm^{-1}$ produces only 1.6% error, it is possible to use the trained model at runtime with a reduced set of wavelengths, such as only ~3% of the original data set, while still retaining a desired amount of decision specificity.

To recap the present description of the linear SVM analysis and the SVM $\beta$ spectrum, the SVM $\beta$ spectra are shown in FIG. 5C (SKH1 mouse skin cancer) and FIG. 5D (human metastatic liver cancer). The spectra resemble IR absorption spectra except that they go up and down (above and below zero). Positive values indicate wavelengths at which the summed contributions of support vectors are most useful for a decision in favor of the defined group (e.g., such as tumor), while negative values indicate those wavelengths most useful for deciding against membership in the defined group. Thus, the most useful wavelengths can be identified, such as to determine the importance of a particular useful wavelength relative to the rest of the wavelengths. The extraction of these SVM $\beta_j$ spectra involved 4,032 and 13,560 training spectra for the mouse tumor and metastatic human liver data, respectively. The noise-to-max-signal percentage using the noise region from 1950-2500 $cm^{-1}$ (avoiding $CO_2$(g) at 2350 $cm^{-1}$) was 13% and 1.8% for the mouse tumor and metastatic human liver data, respectively.

In sum, using thousands of training spectra can be helpful to obtain good signal-to-noise on SVM $\beta$ spectra. Also, even with thousands of training spectra, smoothing was useful for extracting spectral group decision results. While the SVM $\beta_j$ spectrum is helpful for identifying useful wavelengths, it can be noted that these responses are modified by the spectra intensities of the typical group infrared spectra, such as represented in Equation 4, defining the characteristic group decision spectra as $Td_j^+$ or $Td_j^-$ (in FIGS. 5E and 5F). Both the SVM $\beta$ spectra and group decision spectra can vary dramatically with different cancers, as well as with different tissues within the same obtained tissue sample.

To develop decision equations with minimal spectral input, subsets of the input spectral data have been identified, which can give acceptable decisions. Useful wavelengths are offered in Tables 1 and 2 over the full spectral range, scans limited to single 200 $cm^{-1}$ ranges were best when centered at ~1745 and 1085 $cm^{-1}$, and use of only one in every 32 measurements over the full spectral range at 4 $cm^{-1}$ spectral resolution produced only 1.6% error, which may be acceptable in many diagnostic applications.

Further, the present techniques can help enable multi-group (more than two groups) SVM and decision equation imaging, such as for displaying or otherwise presenting richer diagnostic information to a clinician or other user.

Tissue samples can be complex mixtures, and the present technique of multi-group (e.g., one group vs. the rest of all of the other groups) multiclass SVM techniques have been demonstrated with four groups to work very well (e.g., yielding only 1 training error with 20,298 training spectra). The present techniques enable classifying and presenting useful helpful diagnostic information about multiple control groups like lymphocyte-rich and blood-rich regions, as explained above in the illustrative case of metastatic liver cancer. Using linear SVM produces decision equation values with useful information beyond just that needed for classification, as illustrated by the decision equation imaging shown in FIG. 7B. Decision equation imaging provides a useful way of presenting information, such as for the use of IR in medical imaging. The analysis and encoding for imaging display can be configured in any of a variety of desired manners, such as with different sensitivities than tissue staining. As an illustrative example of potential other applications, the present techniques can be used to look for lymphocyte-rich regions in other metastatic liver cancer tissue sections, such as using the decision equations presented and represented as explained herein. While our examples focused on lymphocytes as an additional tissue classification grouping, other cell types and tumor types can additionally or alternatively be similarly classified, such as using the present techniques.

E. Pre-Processing Spectral Data (e.g., Second Derivative, Wavenumber Skipping, Etc.)

As explained with respect to FIG. 2, one or more techniques can be used to pre-process spectral data, such as before using the spectral data for training the learning model 118. Such pre-processing can be applied to the raw spectral data, or to spectral data that has already been pre-processed or transformed, such as into the SVM β spectrum as described above, to which smoothing was applied as pre-processing, such as using the Savitsky-Golay smoothing procedure spanning 20 steps with a $2^{nd}$ order polynomial.

One problem, as mentioned above, can involve inhibiting an effect of water vapor or other gas phase interference on the training of the learning model 118. This can include modifying the spectral data of the training set for training the learning model, such as can include pre-processing of spectral data of the fuller wavelength set using a second derivative of the spectral data across wavenumbers of the fuller wavelength set, used for training, before determining the linear SVM model representation. Such pre-processing using the second derivative of the spectral data can help to inhibit an effect of water vapor or other gas phase interference that may otherwise interfere with using the trained model for evaluating specimen response from the reduced set of illumination wavelengths. Further, the pre-processing using the second derivative can include skipping a specified number of wavenumbers between wavenumbers used to perform the second derivative analysis, such as explained herein.

Figure 11:
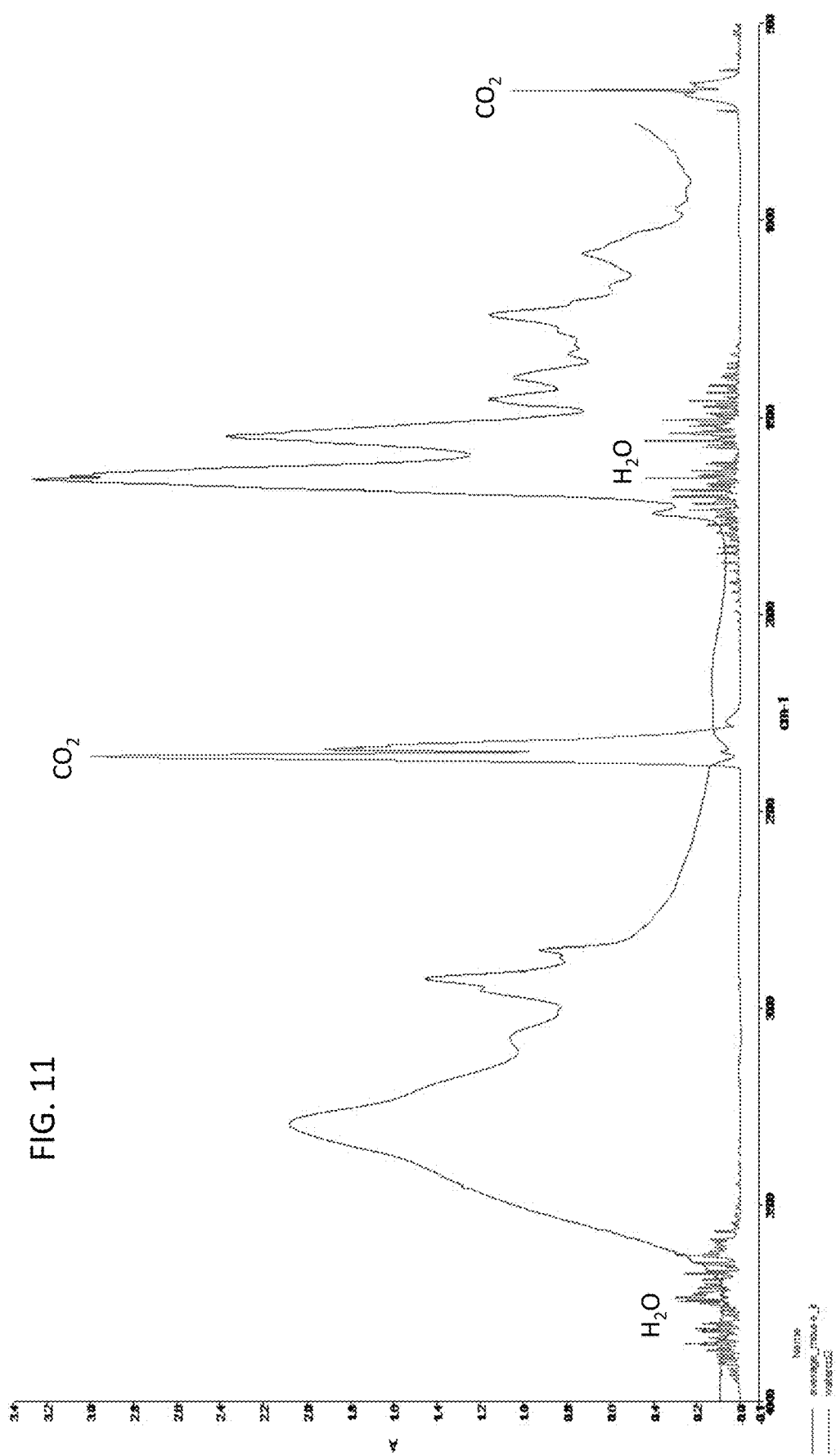
FIG. 11 shows an example of a graph of IR spectral data of attenuation vs. frequency, for a tissue specimen of mouse dermis and epidermis for wavelengths in a range between 500 cm$^{-1}$ and 400 cm$^{-1}$ with a superimposed representation of associated gas phase interference arising from water vapor ($H_2O$) and carbon dioxide ($CO_2$).

FIG. 11 shows an example of a graph of IR spectral data of attenuation vs. frequency, for a tissue specimen of mouse dermis and epidermis for wavelengths in a range between 500 $cm^{-1}$ and 4000 $cm^{-1}$ with a superimposed representation of gas phase interference arising from water vapor ($H_2O$) and carbon dioxide ($CO_2$) associated with the tissue specimen or with an ambient region around the tissue specimen. Without pre-processing, such gas phase interference can affect the spectral analysis of the tissue specimen for tissue discrimination. The present inventors have recognized, among other things, that pre-processing the spectral data, including applying a second derivative to the spectral data, such as a 9-point second derivative, or preferably, a 3-point second derivative, an effect of the gas phase interference on the spectral analysis can be reduced.

Equation 5a provides a general example of a $2^{nd}$ derivative equation.

$$f''(x_i) \approx \frac{\frac{f(x_i + h) - f(x)}{h} - \frac{f(x) - f(x - h)}{h}}{h}, \quad (5a)$$
$$\approx \frac{f(x_i + h) - 2f(x) + f(x - h)}{h^2}$$

Such a second derivative equation can be applied as part of the pre-processing of spectral data. The value of "h" can be selected equal to the interval between wavenumbers in the full IR spectral data set (h=$x_{i+1}$−$x_i$). Letting f($x_i$)=$y_i$ gives the 3 point second derivative of adjacent steps as $$f''(x_i) = \frac{1}{h^2}(y_{i+1} - 2y_i + y_{i-1}). \quad (5b)$$

Figure 13:
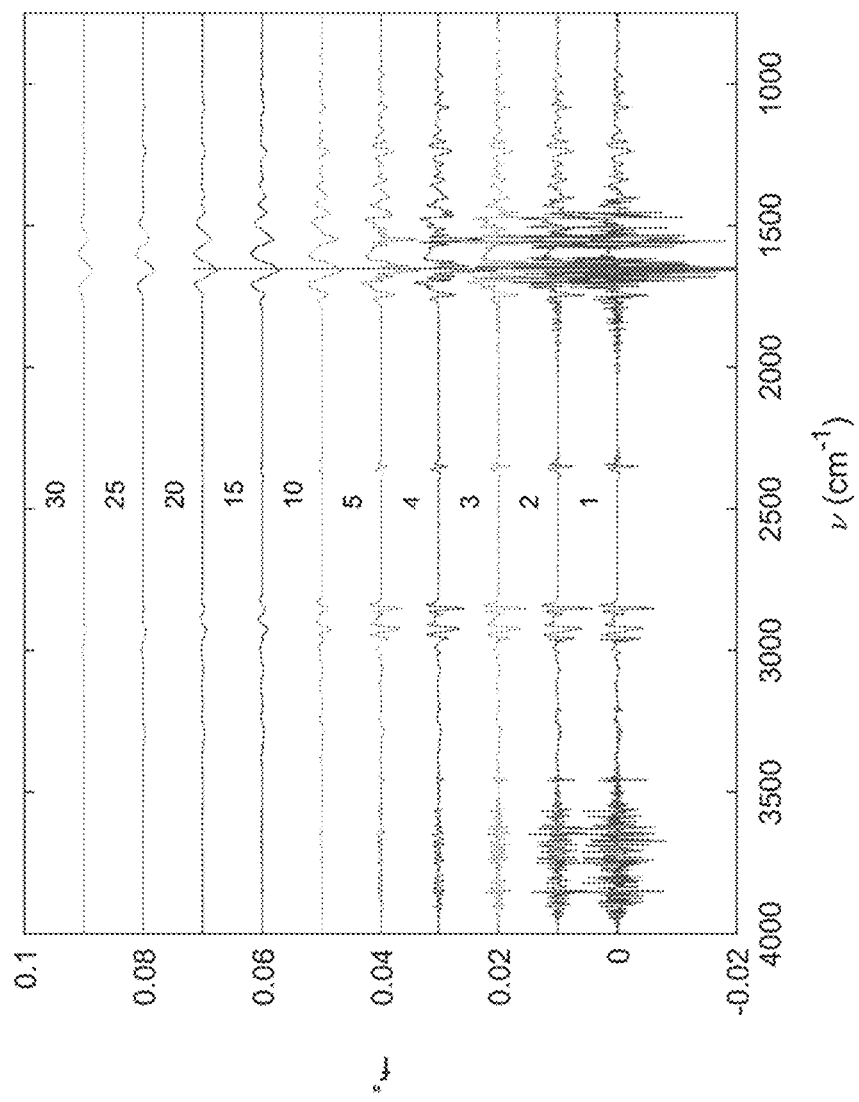
FIG. 13 shows an example of $2^{nd}$ derivatives of spectral data for wavelengths in a range between 500 cm$^{-1}$ and 4000 cm$^{-1}$, using every wavenumber in the data set (steps of 2 cm$^{-1}$, bottom trace), every other wavenumber step (steps of 4 cm$^{-1}$ second trace from bottom), through using every 30 wavenumber steps (60 cm$^{-1}$ steps, top trace).

The result of Equation 5b is shown in FIG. 13 as the bottom blue trace labelled "1". It is dominated by signatures of water vapor. However, the 3 point $2^{nd}$ derivative with steps of 5 h is $$f''(x_i) = \frac{1}{25h^2}(y_{i+5} - 2y_i + y_{i-5}). \quad (5c)$$

The result of Equation 5c is given in FIG. 13 with a green trace labelled "5". It shows the tissue signals with very little water vapor. If one uses larger steps, then both the tissue and water vapor signals are attenuated.

Figure 12:
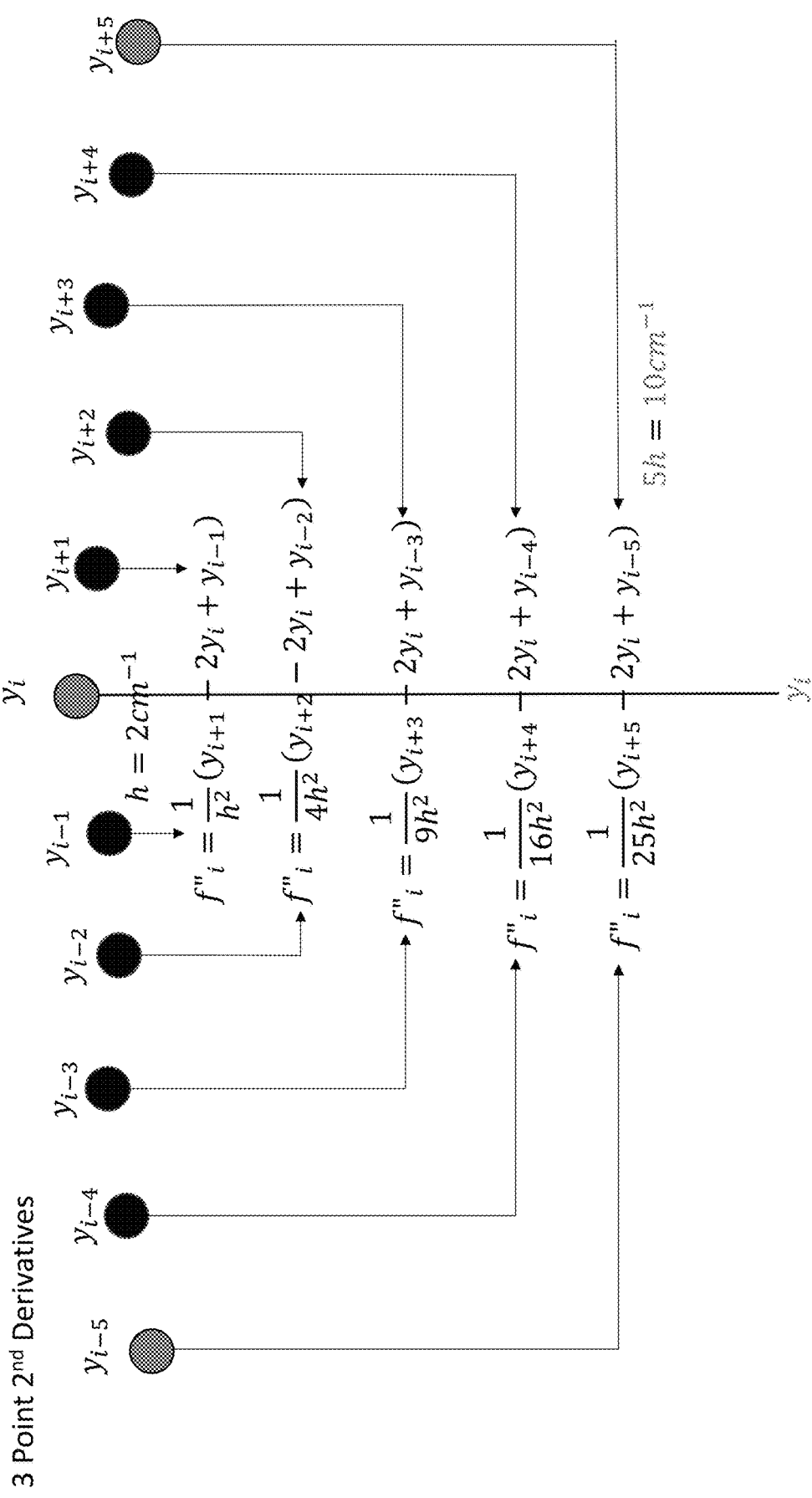
FIG. 12 shows a representation of applying 3-point second derivative pre-processing to IR spectral data at different wavenumber intervals by finite difference equations.

FIG. 12 gives 3 point $2^{nd}$ derivative formulas for steps of h, 2 h, 3 h, 4 h and 5 h. FIG. 12 shows a representation of applying 3-point second derivative pre-processing to IR spectral data at different wavenumber intervals. In FIG. 12, the dots along the top of FIG. 12 represent each adjacent response at adjacent wavenumbers at full resolution (h=2 $cm^{-1}$), while the green dots show only the data used for the 5 h formula (Equation 5c).

FIG. 13 shows an example of $2^{nd}$ derivatives of spectral data for wavelengths in a range between 500 $cm^{-1}$ and 4000 $cm^{-1}$, using every wavenumber in the data set (steps of 2 $cm^{-1}$, bottom trace), every other wavenumber step (steps of 4 $cm^{-1}$ second trace from bottom), through using every 30 wavenumber steps (60 $cm^{-1}$ steps, top trace), Use of the minimum steps gives a $2^{nd}$ derivative dominated by water vapor (bottom trace), while use of 30 steps wipes out all of the response. So there is an optimum near the green trace (labelled 5, representing a 10 $cm^{-1}$ spacing) for detecting tissue without interference from water vapor and minimized attenuation of the tissue signal.

The number that labels each trace is the multiple of h used to calculate the $2^{nd}$ derivative. The bottom blue trace has 1 h=2 $cm^{-1}$, the green trace has 5 h=10 $cm^{-1}$, and the top trace has 30 h=60 $cm^{-1}$. The bottom trace is dominated by the $2^{nd}$ derivative of water vapor, but this signal attenuates as the multiple of h is increased. In this example, the green trace with 5 h=10 $cm^{-1}$ shows an optimal compromise with prominent tissue signal and highly attenuated water vapor signals. If one chooses too high of a multiple then all signals are attenuated which can be seen by the top trace with 30 h=60 cm$^{-1}$. As seen in FIG. 13, optimal filtering occurs with steps of about 5 h=10 cm$^{-1}$. Use of every 5$^{th}$ wavenumber step for performing the second derivative analysis emphasizes the protein dominant regions of the spectral data and attenuates the water vapor interference, which can be very helpful for tissue characterization.

To recap, three-point second derivatives can help provide useful filtering, which has been investigated with a SKH1 mouse skin cancer tissue slice. The average absorption spectrum of mouse skin tissue and its' 2$^{nd}$ derivative by both 3 and 9 point formulas were explored using a data set that was recorded at a resolution of 4 cm$^{-1}$ with 2 cm$^{-1}$ steps. Three point 2$^{nd}$ derivatives were computed (e.g., using Equation 5) with offsets of 1 h, 2 h, 3 h, 4 h, 5 h, 10 h, 15 h, 20 h, 25 h, and 30 h, such as shown in FIG. 13, where h=2 cm$^{-1}$. As seen in FIG. 13, at the lowest offset of 1 data point (2 cm$^{-1}$), the 2$^{nd}$ derivative is dominated by gaseous water. As the digital offset is increased, the gaseous water becomes less prominent and the protein features of the tissue, which provide useful biomolecular differences for tissue classification, are more in evidence. As seen in FIG. 13, for this data, using a 10 cm$^{-1}$ spacing between measured wavenumbers to which the second derivative is applied will provide a very effective filtering of the gas phase water interference. The situation may be even better at a digital offset of 10 or h=20 cm$^{-1}$, but because the output range of the illuminator 109 can be limited (e.g., to about 160 cm$^{-1}$ for a QCL illuminator 109), too large of a digital offset between wavenumbers may limit the available wavenumbers that can be assayed, such as by a particular QCL in a single or multi-QCL illuminator 109.

F. Illuminator Examples: Multiple and Single QCL, Broadband Light Source with Spectral Separation The illuminator 109 (and the response detector 110) can be implemented in various ways and used, individually or in combination, to create the IR spectral data sets, such as for training the learning model 118 or, at run-time, for using the trained learning model to perform tissue classification, as described herein.

Single QCL Illuminator

A tunable mid-infrared quantum cascade laser (QCL) can be used in the illuminator 109, such as can be tuned to permit acquisition of IR absorption or other response data by the response detector 110. The tunable QCL can be tuned, during acquisition of training data, across a fuller set of wavelengths (e.g., all available wavelengths) within an output range of the QCL, for acquiring high resolution spectral data as a training data set for performing the training of a learning model. Training the learning model can include down-selecting from this fuller set of wavelengths to a reduced set of wavelengths, such as for quickly, efficiently, and accurately performing tissue classification at run-time. Such a reduced set of selected IR wavelengths can be optimized during the training, such as for detecting one or more chemical or molecular signatures representative of tissue-specific morphologies, compositions, or characteristics, such as lesions. Illustrative examples of such tissue specific properties that can be classified using the reduced set of wavelengths can include, among others, one or more of cancer, preneoplasia, intracellular accumulations (e.g. steatosis), inflammation, wound healing, or the like.

Multiple QCL Illuminator (e.g., Single Integrated Circuit (IC))

While it is possible to select the reduced set of wavelengths, during training, to fall within the output wavelength range of a single tunable QCL, in certain cases, the system 100 can benefit from the flexibility of an illuminator 108 that can include multiple tunable QCLs, such as with non-overlapping output wavelength ranges (to extend the available range of wavelengths for illumination) or overlapping output wavelength ranges (such as to help provide some redundancy, if desired). While QCLs can be expensive, a multiple QCL integrated circuit (IC) chip can include a substantial number of QCLs (e.g., 32 QCLs) shared on the same monolithic IC. For example, such as 32 QCL on a shared IC illuminator 108 can provide illumination wavelengths from a particular one of the QCLs extending from 1340, 1345, 1350, . . . 1500 cm$^{-1}$, which is a 160 cm$^{-1}$ range with 5 cm$^{-1}$ steps. The 160 cm$^{-1}$ range can be particular to the selected individual QCL chip design. During training, all of the reduced set of wavelengths for tissue classification can be selected to fall within the range of a single QCL of the plurality of available QCLs on the shared monolithic IC. However, the center of the range of the reduced set of wavelengths can be adjusted to any wavenumber from ~2500-625 cm$^{-1}$, in this implementation.

However, the system 100 can use the 32 QCL chip illuminator 108 with two equal sets of 16 wavenumbers each with a 10 cm$^{-1}$ spacing, such as to help provide some redundancy and flexibility of operation. For example, the 32 QCL chip illuminator 108 may have output illumination wavelengths of 1400, 1400, 1410, 1410, . . . 1560, 1560 cm$^{-1}$. This would cover the amide II, III, and IV bands of protein, which are useful spectral ranges for performing spectroscopic tissue classification. The QCL lasers can be fired such as to issue sequential pulses, and can use cooling, if helpful, such as in a similar manner to a single QCL. By providing two QCLs available to issue illumination at each wavenumber, there can be twice the power and frequency at each wavenumber, which can help provide increased sensitivity, but it may be somewhat slower, such as for switching between QCLs in the illuminator 108 issuing the illumination pulses to the tissue specimen 102. The particular center of the wavenumber range can be selected by analyzing a training data set, such as can be obtained from the SKH1 mouse skin data library. In such a configuration, the system 100 can detect all 16 different wavenumbers in parallel, such as using a response detector 110 that can include one or more of an array detector such as a 128 pixel pyroelectric linear array detector, or other suitable photodetector or imaging array detector. The illuminator 108 can optionally be configured to provide chopped signals, such as at a chopping frequency of about 10 Hz, if desired.

Broadband Light Source with Spectral Separator

The illuminator 108 can employ one or more QCLs, such as described above, or can alternatively include a broadband light source configured to permit spectral separation of wavelengths and response detection. Such spectral separation can include using dispersive optics, optical filters, interferometric, or other techniques.

Additional Notes and Variations

Although the above description has emphasized SVM, training of the model 118 can include supervised learning (e.g., classification, regression), unsupervised learning (e.g., clustering, manifold learning, bi-clustering, covariance estimation, density estimation, neural networks) or reinforcement learning. Some illustrative examples of machine learning models can include Random Forest, Support Vector Machines (SVM), stochastic gradient descent, naive Bayes, feature selection, least squares analysis, partial least square analysis, regression models (e.g., linear, logistic, polynomial), multivariate regression (e.g., stepwise, multivariate curve regression, alternating least squares, non-linear), in addition to or as an alternative to the Random Forest technique described above.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A computer-assisted method of discriminating tissue of a specimen, the computer-assisted method comprising:
   receiving and storing electromagnetic energy infrared spectral response data from the specimen in response to delivering illuminating electromagnetic energy to the specimen;
   using a computing device to access a stored trained learning model that has been trained including by storing decision equations represented as (1) a $\beta$ spectrum that includes the summed response of all support vectors at each spectral training wavelength of the trained learning model, (2) an average or other central tendency of training spectra, (3) a standard deviation or other spread of the training spectra, and (4) a bias or offset constant, and applying the trained learning model to the stored electromagnetic energy infrared spectral response data for classifying one or more locations of the specimen into a classification including at least one of at least three available categories including (1) a tumor category; (2) a non-tumor category; and (3) a histology category that is different from a tumor category and different from a non-tumor category; and
   using the computing device, generating an indication for display to the user for visually differentiating according to the at least three available tissue classification categories.

2. The computer-assisted method of claim 1, wherein the histology category includes at least one of the following histology subcategories:
   a blood-dominated tissue histology subcategory;
   a non-blood-dominated tissue histology subcategory;
   a basal tissue histology subcategory;
   a squamous tissue histology subcategory;
   a lymphocyte-rich tissue histology subcategory;
   a non-lymphocyte-rich tissue histology subcategory;
   a keratinous tissue histology subcategory; or
   a non-keratinous tissue histology subcategory.

3. The computer-assisted method of claim 1, wherein receiving the electromagnetic energy response data from the specimen includes using an Attenuated Total Reflection (ATR) probe.

4. The computer-assisted method of claim 1, wherein:
receiving and storing the electromagnetic energy response data from the specimen includes receiving electromagnetic energy response data from different locations of the specimen at an imaging focal plane array (FPA) including pixels corresponding to the electromagnetic energy response data from the different locations of the specimen;
the classifying includes, using the computing device, classifying individual pixels using the trained learning model and the stored electromagnetic energy response data to categorize an individual pixel into one of the at least three categories; and
providing, via the computing device and an output pixel array, a color imaging representation of the classified individual pixels, using different colors of individual pixels in the output pixel array to represent the different ones of the categories, and using an intensity indication of the individual pixels in the output pixel array to represent classification strength information from the trained learning model.

5. The computer-assisted method of claim 1, wherein the delivering illuminating electromagnetic energy to the specimen includes delivering electromagnetic energy including at least one of selecting or tuning or adjusting at least one of (1) a Quantum Cascade Laser (QCL) or (2) a broadband light source that is configured to permit spectral separation before the delivering.

6. The computer-assisted method of claim 1, wherein the learning model is trained using a fuller wavelength set, relative to a reduced wavelength set for delivering the illuminating electromagnetic energy to the specimen, and wherein delivering the illuminating electromagnetic energy to the specimen for the classifying and the providing the tissue output classification indication includes using a reduced wavelength set relative to the fuller wavelength set.

7. The computer-assisted method of claim 6, wherein using the trained model includes using a trained model representation that includes at least: (1) a $\beta$ spectrum including the fuller wavelength set; (2) a central tendency indicator ($\mu$) of the training set; (3) a spread indicator ($\sigma$) of the training set; and (4) a scaling factor.

8. The computer-assisted method of claim 7, wherein the trained model representation is represented according to:

$$d_k = b + \left(\left|\frac{Test_{k,j} - \overline{Train_j}}{\sigma_{Train_j}}\right| \beta_j\right), \text{ where}$$

$$\beta_j = \sum_i \alpha_i y_i \left(\frac{SV_{i,j} - \overline{Train_j}}{\sigma_{Train_j}}\right),$$

wherein $d_k$ represents one of k decision equations or other classifier criteria, b is an offset constant, $\beta_j$ is referred to as a "beta spectrum", $\overline{Train_j}$ represents an average of a training set, and $\sigma_{Train_j}$ represents a standard deviation or other spread indicator of the training set.

9. A computer-assisted method of discriminating tissue of a specimen, the method comprising:
receiving and storing electromagnetic energy response data, the electromagnetic energy response data obtained from a location of the specimen in response to illuminating the specimen according to a specified electromagnetic energy illumination reduced wavelength set that is reduced with respect to a fuller wavelength set used for training a linear Support Vector Machines (SVM) model using a computing device and a training set based on the stored electromagnetic energy response data;
obtaining decision equations from the trained linear SVM model, using the computing device, with the trained linear SVM model providing the decision equations based on a linear SVM model representation;
applying the obtained decision equations to the received electromagnetic energy response data corresponding to the reduced wavelength set, using the computing device, for discriminating between at least two tissue categories of the location of the specimen; and
using the computing device, generating an indication for display to the user for visually differentiating according to the at least three available tissue classification categories.

10. The computer-assisted method of claim 9, wherein the linear SVM model representation includes at least: (1) a stored SVM $\beta$ spectrum including the fuller wavelength set used for training the linear SVM model representation; (2) a central tendency indicator ($\mu$) of the training set; (3) a spread indicator ($\sigma$) of the training set; and (4) a scaling factor.

11. The computer-assisted method of claim 9, wherein the electromagnetic energy response data is obtained from the location of the specimen in response to illuminating the specimen according to a specified electromagnetic energy illumination reduced wavelength set using a selectable tunable Quantum Cascade Laser (QCL), wherein the reduced wavelength set is specified to correspond to wavelengths falling within an output wavelength range of the selectable QCL.

12. The computer-assisted method of claim 11, wherein the electromagnetic energy response data is obtained from the location of the specimen in response to illuminating the specimen according to a specified electromagnetic energy illumination reduced wavelength set using a single tunable Quantum Cascade Laser (QCL), wherein the reduced wavelength set is specified to correspond to wavelengths falling within an output wavelength range of the single QCL.

13. The computer-assisted method of claim 9, wherein the electromagnetic energy response data is obtained from the location of the specimen in response to illuminating the specimen according to a specified electromagnetic energy illumination reduced wavelength set using broadband light source configured to permit spectral separation before delivery to the specimen.

14. The computer-assisted method of claim 9, wherein the training set includes, using the computing device, pre-processing of spectral data of the fuller wavelength set using a second derivative of the spectral data across wavenumbers of the fuller wavelength set before determining the linear SVM model representation to help inhibit an effect of water vapor or other gas phase interference.

15. The computer-assisted method of claim 14, wherein the second derivative of the spectral data across wavenumbers of the fuller wavelength set includes, using the computing device, skipping one or more steps of wavenumbers for performing the second derivative.

16. The computer-assisted method of claim 15, wherein the skipping wavenumbers includes, using the computing device, skipping steps of wavenumbers includes skipping between 1 and 4 steps of wavenumbers between steps of wavenumbers selected for performing the second derivative.

17. The computer-assisted method of claim 9, wherein the decision equations include more than two decision equations corresponding to respective tissue classification categories.

18. The computer-assisted method of claim 17, wherein the histology category includes at least two mutually-exclusive histology subcategories.

19. The computer-assisted method of claim 9, wherein the electromagnetic energy response data is obtained from various locations within an area of the specimen.

20. The computer-assisted method of claim 19, further comprising, using the computing device, generating an image of the area for display to a user, the image visually differentiating displayed locations in the area according to the at least two categories.

21. The computer-assisted method of claim 20, further comprising, using the computing device, generating the image of the area for display to the user, the image visually differentiating using different colors or shading of displayed locations in the area according to more than two tissue classification categories.

22. The computer-assisted method of claim 20, further comprising the visually differentiating including using pixels representing the displayed locations in the area with corresponding pixel intensities based on a strength indication provided by the computing device using the decision equations.

23. A computer-assisted method of discriminating tissue of a specimen, the method comprising:
receiving and storing electromagnetic energy response data, the electromagnetic energy response data obtained from a location of the specimen in response to illuminating the specimen according to a specified electromagnetic energy illumination reduced wavelength set that is reduced with respect to a fuller wavelength set used for training a linear or non-linear SVM model using a training set and a computing device;
using the computing device, accessing a stored representation of the trained SVM model that has been trained including by storing decision equations represented as (1) a β spectrum that includes the summed response of all support vectors at each spectral training wavelength, (2) an average or other central tendency of training spectra, (3) a standard deviation or other spread of the training spectra, and (4) a bias or offset constant, and obtaining more than two decision equations from the trained SVM model; and
using the computing device, applying the obtained more than two decision equations from the trained SVM model to the received electromagnetic energy response data corresponding to the reduced wavelength set, discriminating between more than two tissue classification categories of the location of the specimen; and
using the computing device, generating an indication for display to the user for visually differentiating according to the at least three available tissue classification categories.

24. A computer-assisted method of claim 23, further comprising, using the computing device, generating an image of the area for display to a user, the image visually differentiating displayed locations in the area according to the classifying.

25. The computer-assisted method of claim 24, further comprising, using the computing device, generating the image of the area for display to the user, the image visually differentiating using different colors or shading of displayed locations in the area according to corresponding particular categories.

26. The method of claim 25, further comprising, using the computing device, generating the image of the area for display to the user, the image visually differentiating using at least one of different colors or color intensities or shading of displayed locations in the area corresponding to different cell morphologies.

27. A computer-assisted method of discriminating tissue of a specimen, the method comprising:
receiving and storing electromagnetic energy response data, the electromagnetic energy response data obtained from a location of the specimen in response to illuminating the specimen according to a specified electromagnetic energy illumination reduced wavelength set that is reduced with respect to a fuller wavelength set used for training a model using a training set and a computing device;
using the computing device, obtaining decision equations from the trained model, the trained model providing the decision equations based on a model representation;
using the computing device, applying the obtained decision equations to the received electromagnetic energy response data corresponding to the reduced wavelength set, discriminating between at least two categories of the location of the specimen, the discriminating including classifying one or more locations of the specimen into a classification including at least one of at least three available categories including (1) a tumor category; (2) a non-tumor category; and (3) a histology category that is different from a tumor category and different from a non-tumor category;
wherein the training set includes a pre-processing of spectral data of the fuller wavelength set using a second derivative of the spectral data across wavenumbers of the fuller wavelength set before determining the model representation to help inhibit an effect of water vapor or other gas phase interference; and
wherein the trained model is stored on a computer-readable medium, and wherein a representation of the trained model includes decision equations stored as at least: (1) a β spectrum including the fuller wavelength set; (2) a central tendency indicator (μ) of the training set; (3) a spread indicator (σ) of the training set; and (4) a scaling factor, and wherein the trained model representation is further represented according to:

$$d_k = b + \left(\frac{Test_{k,j} - \overline{Train_j}}{\sigma_{Train_j}} \middle| \beta_j\right), \text{ where}$$

$$\beta_j = \sum_i \alpha_i y_i \left(\frac{SV_{i,j} - \overline{Train_j}}{\sigma_{Train_j}}\right),$$

wherein $d_k$ represents one of k decision equations or other classifier criteria, b is an offset constant, $\beta_j$ is referred to as a "beta spectrum", $\overline{Train_j}$ represents an average of a training set, and $\sigma_{Train_j}$ represents a standard deviation or other spread indicator of the training set; and
using the computing device, generating an indication for display to the user for visually differentiating according to the at least three available tissue classification categories.

28. The computer-assisted method of claim 27, wherein using the second derivative of the spectral data across wavenumbers of the fuller wavelength set includes, using the computing device, skipping steps of wavenumbers for performing the second derivative.

29. The computer-assisted method of claim 28, wherein the skipping steps of wavenumbers includes, using the computing device, skipping steps of between 1 and 4 wavenumbers between wavenumbers selected for performing the second derivative.

\* \* \* \* \*